(12) United States Patent
 Rzigalinski et al.

(10) Patent No.: US 8,747,907 B2
(45) Date of Patent: Jun. 10, 2014

(54) ANTI-INFLAMMATORY, RADIOPROTECTIVE, AND LONGEVITY ENHANCING CAPABILITIES OF CERIUMOXIDE NANOPARTICLES

(76) Inventors: Beverly A. Rzigalinski, Radford, VA (US); Ariane M. Clark, Bradenton, FL (US)

( * ) Notice: Subject to any disclaimer, the term of this patent is extended or adjusted under 35 U.S.C. 154(b) by 0 days.

(21) Appl. No.: 13/539,564

(22) Filed: Jul. 2, 2012

(65) Prior Publication Data
US 2013/0004584 A1      Jan. 3, 2013

Related U.S. Application Data

(63) Continuation of application No. 11/993,260, filed as application No. PCT/US2006/024963 on Jun. 27, 2006, now abandoned.

(60) Provisional application No. 60/693,930, filed on Jun. 27, 2005.

(51) Int. Cl.
*A01N 59/16* (2006.01)
*A61K 33/24* (2006.01)

(52) U.S. Cl.
USPC ........... 424/617; 435/375; 977/773; 977/811; 977/915

(58) Field of Classification Search
None
See application file for complete search history.

(56) References Cited

U.S. PATENT DOCUMENTS 7,534,453 B1 * 5/2009 Rzigalinski et al. .......... 424/617
2002/0110519 A1 * 8/2002 Ying et al. .................... 423/600

OTHER PUBLICATIONS

Unknown. 2003. UCF brain cell research spawns hope for longer life. Eurekalert [online]; downloaded from URL <http://www.eurekalert.org/pub_releases/2003-08/uocf-ubc081303.php> on Jan. 2, 2013; 2 pages.*
Thompson C. 2004. Nanoparticles pop up everywhere. Discover Magazine [online]; downloaded from URL <http://discovermagazine.com/2004/jan/technology> on Jan. 2, 2013; 2 pages.*

* cited by examiner

*Primary Examiner* — Carlos Azpuru
*Assistant Examiner* — David Browe
(74) *Attorney, Agent, or Firm* — Tarolli, Sundheim, Covell & Tummino LLP

(57) ABSTRACT

The present invention provides cerium oxide nanoparticles for use both in therapeutic compositions in vivo and in research in vitro. The cerium oxide nanoparticles are of known range of sizes having biological properties that are reproducible and beneficial. Pharmaceutical and other compositions are provided, as are methods of treatment.

21 Claims, 27 Drawing Sheets

ANTI-INFLAMMATORY, RADIOPROTECTIVE, AND LONGEVITY ENHANCING CAPABILITIES OF CERIUMOXIDE NANOPARTICLES

This application is a continuation of U.S. patent application Ser. No. 11/993,260, filed Mar. 4, 2010 now abandoned, which is a U.S. National Stage Application of PCT/US2006/024963, filed Jun. 27, 2006, which claims priority to U.S. Provisional Patent Application Ser. No. 60/693,930, filed Jun. 27, 2005. This application incorporates the above-identified applications herein by reference in their entirety and claims priority to all aforementioned applications for all purposes.

STATEMENT OF GOVERNMENT INTEREST

This invention was made partially with U.S. Government support from the United States National Institutes of Health under Contract No. NS40490 (National. Institute of Neurological Disorders & Stroke) and AG022617 (National Institute on Aging). The U.S. Government has certain rights in the invention.

BACKGROUND OF THE INVENTION

1. Field of the Invention

The present invention relates to the field of medicine and treatment of medically relevant diseases, disorders, and complications of injury, inflammation, and aging More specifically, the invention relates to the use of nanoparticles to treat subjects suffering from various diseases, disorders, and complications due to injury, inflammation, radiation exposure, and aging.

2. Description of Related Art

Many approaches have been taken to treat, either therapeutically or prophylactically, diseases, disorders, and other medically important conditions that have, as a major component, cell injury or death due to free radicals, such as oxygen radicals. Among those approaches were the use of free radical scavengers, such as Vitamin E and its related compounds, Vitamin C and its related compounds, and melatonin, to name a few. While beneficial effects of these compounds has been noted, researchers and clinicians continue to search for compounds with higher activities and half-lives.

In early experiments performed by the present inventors and their colleagues, cerium oxide nanoparticles prepared by a sol-gel process were utilized to enhance cell longevity. The cerium oxide nanoparticles were proposed to act as free radical scavengers to bring about the observed results. However, the sol-gel process posed several difficulties. For example, particle size was not well-controlled within the reported 2-10 nm range, making variability between batches high. That is, the process, while satisfactory for producing nanoparticles with free radical scavenging activity, did not reproducibly produce particles of a specific size range. Thus, each batch of particles needed to be tested to confirm the size range and the suitability of the batch for use. In addition, the process resulted in tailing of surfactants used in the process into the final product. The presence of these surfactants produced biological difficulties when used, primarily due to the toxicity of the surfactants in the product. Furthermore, the inability to control the amount of surfactant tailing posed problems with agglomeration when nanoparticles were placed in biological media. These difficulties reduced particle efficacy and biological deliverability. Removal of surfactant after sol-gel synthesis produced particles that appeared prone to agglomeration in biological media, and had a lack of biological effects.

Further, difficulties were encountered with changes in valence state of cerium associated with these particles, causing alterations in the ratio of valence states of cerium (+3/+4) that occurred over time, particularly when particles were placed in biological media. It is possible that the +3/+4 ratio of valence states in the nanoparticles might alter free radical scavenging and cellular delivery, including delivery in vivo.

Thus, while the previous solution to use nanoparticles as free radical scavengers was effective, it was highly variable from batch to batch. Therefore, a need in the art still exists for unproved nanoparticles and methods of use of those particles to treat various diseases and disorders involving production of oxygen radicals and other radicals.

SUMMARY OF THE INVENTION

The present invention addresses this need in the art by providing a method for the use of cerium oxide nanoparticles in health. As a general matter, the method extends the life of a living cell by exposing the cell to cerium oxide nanoparticles. This exposure reduces or eliminates damage to the cell caused by endogenous and exogenous free radicals. The cerium oxide nanoparticles can be exposed to the cell before, during, or after free radical image.

Broadly speaking, the present invention provides a method of treating at least one cell with cerium oxide particles. The method generally comprises contacting at least one cell with an amount of cerium oxide nanoparticles that reduces or eliminates damage caused by free radicals. The method can be practiced in vivo as either a therapeutic method of treating a disease or disorder involving free radicals or as a prophylactic method to prevent free radical damage. Likewise, the method can be practiced in vitro as a research tool to study the effects of free radicals on cells or the effects of combinations of nanoparticles with drugs on cells. In preferred embodiments, the method is practiced with size-limited cerium oxide nanoparticles made by a method other than a sol-gel method. The method can also be practiced ex vivo or in vitro for therapeutic or research purposes.

The present invention provides methods of treating individuals suffering from, or suspected of suffering from, a disease or disorder involving free radicals, such as oxygen radicals. It likewise provides methods of treating individuals suffering from, or suspected of suffering from a complication of an injury that results from free radicals, such as oxygen radicals, or results in the production of free radicals, such as oxygen radicals. In general, the methods of the invention comprise administering to an individual (used interchangeably herein with "subject" and "patient") an amount of cerium oxide nanoparticles sufficient to reduce or eliminate cell, tissue, or organ damage in the individual that is caused by free radicals. Thus, the invention encompasses the use of cerium oxide nanoparticles in enhancement of cell and organism longevity, reduction of inflammation and inflammatory disorders, reduction in tissue damage due to inflammatory disorders, and reduction in radiation injury.

In a further aspect, cerium oxide nanoparticles and compositions comprising cerium oxide nanoparticles are provided. The cerium oxide nanoparticles are size-limited and provided in an amount sufficient to provide one or more doses to a subject in need of, or suspected of being in need of, treatment for a disease or disorder involving free radicals. Compositions may comprise cerium oxide particles of the invention along with one or more other substances, which are typically substances that are biologically tolerable in that they may be exposed to living cells without killing the cells. In embodiments, the other substances are pharmaceutically acceptable substances.

Certain aspects of the invention provide for the use of cerium oxide nanoparticles in the treatment of diseases and disorders associated with free radicals, such as oxygen free radicals. The use is in particular for in vivo therapeutic or prophylactic methods of protecting cells from free radical damage. Certain other aspects of the invention provide for the use of cerium oxide nanoparticles in the preparation of compositions for medical use, such as pharmaceutical or therapeutic compositions.

Another aspect of the invention provides a container containing cerium oxide nanoparticles. In general, a container according to the invention contains a sufficient amount of size-limited cerium oxide nanoparticles made by a method other than a sol-gel method to provide at least one dose of cerium oxide to a subject suffering from, or at risk of suffering from, a disease or disorder involving free radicals, such as oxygen radicals. In certain embodiments, the container is provided in a package with one or more other containers and/or with one or more articles of manufacture or devices having use in delivery of substances to subjects (e.g., syringes, needles, antiseptic swabs). In some embodiments, kits comprising one or more containers are provided. In some kits, single dose amounts of cerium oxide particles are provided. In some embodiments, the single dose is 1 ng to 100 mg per kg weight of subject.

BRIEF DESCRIPTION OF THE DRAWINGS

The accompanying drawings, which are incorporated in and constitute a part of this specification, illustrate several embodiments of the invention and, together with the written description, serve to explain principles of the invention.

DETAILED DESCRIPTION OF VARIOUS EMBODIMENTS OF THE INVENTION

Figure 1:
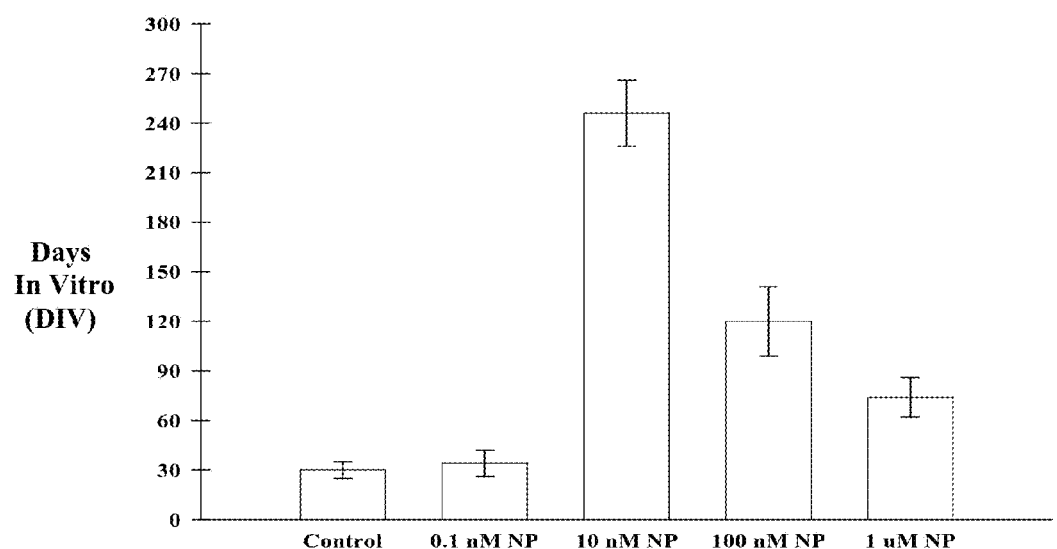
FIG. 1 depicts the effects of cerium oxide nanoparticles on the maximum lifespan of mixed neuronal cells in culture.

Reference will now be wide in detail to various exemplary embodiments of the invention, examples of which are illustrated in the accompanying drawings. The following detailed description is provided to give details on certain embodiments of the invention, and should not be understood as a limitation on the full scope of the invention.

A present inventor and her colleagues previously developed cerium oxide nanoparticles for treatment of various diseases and disorders, which was disclosed in U.S. provisional patent application No. 60/408,275 and in a U.S. non-provisional patent application filed on 4 Sep. 2003 under Ser. No. 10/655,143, the entire disclosures of both of which are hereby incorporated herein by reference. To address the shortcomings of prior attempts to develop cerium oxide nanoparticles for use in treating damage caused by free radicals, different methods of synthesizing nanoparticles, and thus different nanoparticles, were investigated. Efforts were directed toward examining the biological efficacy of commercially available cerium oxide nanoparticles prepared by existing manufacturing processes. These included cerium oxide nanoparticles available from Nanophase Technologies Corporation (Romeoville, Ill.), Advanced Powder Technology Pty Ltd. (Welshpool, Western Australia), and NanoScale Materials Inc. (Manhattan, Kans.). In summary, in a series of experiments, it was found that cerium oxide nanoparticles produced by Nanophase Technology Corporation, using specific, patented mechanisms of synthesis, provided consistently reproducibly sized nanoparticles that consistently showed high levels of biological activity. With sizes of 20 nm and below, particles readily entered cells and reduced free-radical mediated damage. Synthesis for these particles has been described in the following patents, the disclosures of the entireties of all of which are incorporated herein by reference: U.S. Pat. Nos. 6,669,823, 5,460,701, 5,514,349, 5,874,684, Japanese Patents JP2980987 and JP3383608, European Patent EP0711217B1, German Patent DE69426886, French Patent FR94922757, Great Britain Patent GB94922757, and Australian Patent AU068582882.

It was surprisingly found that the new source of cerium oxide nanoparticles, as compared to those of the inventor's prior invention, provided superior reproducibility of activity from batch to batch, and showed lower toxicity to mammalian cells. It was determined that the cerium oxide nanoparticles used in the present invention were different from the prior nanoparticles in quality and size distribution, factors that significantly contribute to their improved characteristics in treating subjects according to the methods of the invention. In developing the invention, it was determined that, regardless of source, cerium oxide particles having a small size, narrow size distribution, and low agglomeration rate are most advantageous. Also, for delivery, the nanoparticles are advantageously in a non-agglomerated form. To accomplish this, stock solutions of about 10% by weight can be sonicated in ultra-high purity water (16 megaohms) or in normal saline prepared with ultra high purity water. These nanoparticles are superior to previously developed cerium oxide nanoparticles for treatment of, and protection against, damage caused by free radicals. This new and useful improvement allows cerium oxide nanoparticles to be used in extending the life of a cell in vivo as well as in vitro. In particular, it is shown herein the novel finding that cerium oxide nanoparticles of a defined size range and distribution and made by a method other than sol-gel synthesis increase the lifespan of cells, such as cells of an organism in vivo. Also shown is that cerium oxide nanoparticles enhance the lifespan of mammalian cells in culture and in vivo, act as potent free radical scavengers, and possess significant anti-inflammatory and radioprotective properties in vivo.

While not wishing to be limited to any single method of action, it is thought that cerium oxide nanoparticles have a unique oxide lattice and valence structure that might confer them with the ability to scavenge (detoxify) intracellular free radicals, and might thus convey their anti-inflammatory, radioprotective, and longevity-enhancing properties. Further, the data obtained by the inventors, and provided herein, suggests that the valence and oxygen lattice structure conveys the ability of cerium oxide nanoparticles to regenerate a biologically active matrix after a free radical scavenging event. This allows small, single doses of nanoparticles to remain active within the cell for long periods of time, conveying regenerative biological effects. In contrast, most commonly available free radical scavengers, such as vitamin E, nitrosone compounds, and vitamin C are inactivated by alteration of their chemical structure after scavenging a single free radical. This loss of structure limits their pharmacological efficacy and requires high dosing regimens.

It appears that the regenerative activity of the cerium oxide nanoparticles may be dependent on a well-known oscillating chemical phenomenon, known as the Belousov-Zhabotinsky (B-Z) reaction, in which cerium oxide serves to facilitate oscillation of electrons (or free radicals) from one compound to another. Cerium in the nanoparticles exists in two valence states, +3 and +4. Adequate propagation of B-Z requires a specific ratio of Ce+3 to +4 in the nanoparticles. If the composition changes to have too much +3 cerium, the reaction will not propagate. Research has shown that as the cerium oxide nanoparticle size is reduced from 30 nm to 3 nm, lattice strain in the nanoparticles causes more cerium to be in the +3 state. Although this mechanism has only been studied in vitro up to now, this mechanism of action may also be true in vivo and would provide a significant advantage to using larger sizes of cerium oxide nanoparticles.

Broadly speaking, the present invention provides a method of treating at least one cell with cerium oxide particles. The method generally comprises contacting at least one cell with an amount of cerium oxide nanoparticles that reduces or eliminates damage caused by free radicals, which are unstable, highly reactive molecules such as nitric oxide, superoxide, hydroxyl radicals, peroxynitrite, and other unstable reactive compound formed from the above. They cause aging and various diseases by taking electrons from other molecules in the body, a process that causes cell or oxidative damage. As used herein, cell or oxidative damage has the same meaning as oxidative stress.

Contacting means any action that results in at least one cerium oxide nanoparticle physically contacting at least one cell. It thus may comprise exposing the cell(s) to cerium oxide nanoparticles in an amount sufficient to result in contact of at least one cerium oxide nanoparticle with at least one cell. The method can be practiced in vivo, in which ease contacting means exposing at least one cell in a subject to at least one cerium oxide nanoparticle. According to the invention, contacting thus may comprise exposing at least one cell to at least one cerium oxide particles, such as, for example by administering cerium oxide particles to a subject via any suitable route. It also may comprise exposing cells in vitro or ex vivo by introducing, and preferably mixing, cerium oxide particles and cells in a controlled environment, such as a culture dish or tube. Optionally, where practiced in vitro or ex vivo, some or all of the cerium oxide particles that are not taken up or adsorbed by cells are removed, for example by washing the cells in suitable media, buffer, water, etc. According to the invention, contacting may comprise introducing, exposing, etc. the cerium oxide particles at a site distant to the cells to be contacted, and allowing the bodily functions of the subject, or natural (e.g., diffusion) or man-induced (e.g., swirling) movements of fluids to result in contact of the nanoparticle(s) and cell(s). Where practiced ex vivo, the cells may also be re-introduced into a subject, preferably the subject from which they were originally obtained. In one embodiment, this includes putting the particles into a gel or other packet that limits diffusion, followed by implanting it into a body area such as a knee joint.

According to the method of the invention, the subject, individual, or patient can be any organism to whom the cerium oxide nanoparticles are administered. Thus, the subject may be a human or a non-human animal, such as another mammal, including, but not limited to a rodent (e.g., mouse, rat, rabbit), a canine (e.g., a dog), a feline (e.g., a cat), an equine (e.g., a horse), an ovine (e.g., a sheep), an orcine (e.g., a pig), or a bovine (e.g., a cow or steer). The subject can be any other animal such as a bird, reptile, amphibian, or any other companion or agricultural animal.

The method can be practiced in vivo as either a therapeutic method of treating a disease or disorder involving free radicals or as a prophylactic method to prevent free radical damage. In embodiments where the method is a method of treating e., a therapeutic method), the amount is an amount that is effective for reducing or eliminating cell death or dysfunction or tissue or organ damage due to free radicals that are being produce, or were produced previously, in the subject. The subject, individual, or patient may be one who is in immediate or apparent need of or suspected of being in need of treatment for a disease or disorder associated with free radicals, or it may be one who is in immediate or apparent need of, or suspected of being in need of, treatment for an injury or other trauma resulting from or known to result in production of free radicals. In such situations, where a pre-existing condition related to cell, tissue, or organ damage due to free radicals is evident or suspected, the method is a therapeutic method. For example, if a subject has had a stroke, it may be beneficial to treat the subject with cerium oxide nanoparticles to reduce the effects of the stroke.

In addition, according to the methods of the invention, the subject, individual, or patient may be one who is not in or suspected of being in need of treatment of a pre-existing disease, disorder, or injury or trauma. In such situations, the method is a prophylactic method. Prophylactic methods are useful in situations where the subject is currently engaged in, or soon to be engaged in, one or more activities that might result in an injury or trauma. They are also useful in situations where the patient has a likelihood of developing a disease or disorder associated with cell, tissue, or organ damage due to free radicals. Thus, the present methods are useful not only for treating patients with a disease or disorder, but for treating patients who are suspected of having a predisposition to a disease or disorder. For example, if the family of a subject has been shown to be prone to a certain neurodegenerative disease, the subject may be given cerium oxide nanoparticles to avoid or reduce the effects of that disease. Likewise, if a subject suspects he will be exposed to high levels of radiation, such as a worker in the nuclear energy or weapons industries, or a person about to go on a vacation in which he will be exposed to high levels of sunlight and its UV component, may be treated with the cerium oxide nanoparticles of the invention. In another example, military uniforms, including clothes and helmets, can be made containing cerium oxide nanoparticles to scavenge free electrons and gamma irradiation for troops exposed to potential radiation.

As another example to compare prophylactic and therapeutic methods, in embodiments where the method is a prophylactic method, the amount is an amount that is effective in reducing or blocking cell death or dysfunction or tissue or organ damage due to free radicals that might be produced in the subject in the future. For example, in a therapeutic method, the cerium oxide nanoparticles may be administered to a patient following a head injury to reduce the amount of damage to the brain as a result of the injury. In contrast, in a prophylactic method, the cerium oxide nanoparticles may be administered to a subject prior to engaging in an activity that has a likelihood of head injury, such as a car race or other high-speed activity.

The act of administering cerium oxide nanoparticles can be any act that provides the cerium oxide nanoparticles to a subject such that the particles can function for their intended purpose. For example, administering can be by injection or infusion. It can thus be an intramuscular, intraparatoneal, subcutaneous, or intrathecal injection, or a slow-drip or bolus infusion. Other non-limiting examples of methods of administration include topical administration, such as by way of lotions, salves, or bandages, often on intact skin but also through open wounds, lesions, or sores. Yet other non-limiting examples include administration through mucous membranes, such as by way of intranasal administration through inhalation of dry particles or a mist comprising the particles, oral ingestion, sublingual absorption, by subcutaneous means, and rectal or vaginal delivery. The vehicle of delivery may be in any suitable form, such as the form of an oral solution, gel, tablet, capsule, powder, suppository, infusible, losenge, cream, lotion, salve, inhalant, or injection.

According to embodiments of the method, the method can comprise repeating the act of contacting (e.g., administering) the cerium oxide nanoparticles. In embodiments relating to administering the cerium oxide to subjects, repeating the administration can include one or more administrations in addition to the original administration. The amount to be administered to each subject will vary depending on usual factors taken into consideration for dosing of pharmaceuticals, such as weight, general health, and metabolic activities of the patient. Likewise, the mode of administration (e.g., injection, oral administration) will be taken into account when determining the proper amount of nanoparticles to administer per dose.

In general, a dosing of about 0.01 ng to about 1 g, such as about 0.05 ng, 0.1 ng, 0.5 ng, 1 ng, 10 ng, 50 ng, 100 ng, 500 ng, 1 ug, 5 ug, 10 ug, 50 ug, 100 ug, 500 ug, or 1 g per administration or per kg body mass per administration should be effective in providing the desired therapeutic or prophylactic result. Of course, injection or infusion amounts will tend to be on the lower end of the range while oral administration amounts will tend to be on the upper end. Current results suggest that the optimal dose for 20 nm cerium oxide nanoparticles is 10 nM to 1 uM for blood and intracellular fluid levels. However, the action of the particles is highly dependent on other variables and so these amounts will vary depending on the surface area, the species of the subject, the reason for administration etc. Amounts may be higher when the method is practiced in vitro or ex vivo because excess particles may be easily removed at any time by washing, etc.

It should be noted that this method shows low toxicity in mammalian cells, fruit flies, and mice, and thus is expected to show low toxicity in other animal cells. This new and useful improvement allows the method of the present invention to be used in subjects with lower toxicity than in previous inventions. This important feature of the present invention means that the cerium oxide nanoparticles can be used in a broad range of applications. In preferred embodiments, the cerium oxide nanoparticles do not contain docusate sodium, which has been shown to produce toxicity in tissue culture. Also, in preferred embodiments, there are less than 1% (w/w or w/v) of any other contaminating ions, metals, or other substances, which can also cause toxicity to cells.

Although the cerium oxide nanoparticles show very low toxicity, in some instances it might be desirable to provide multiple, low doses of particles to an individual. In such cases, the method may comprise two or more administrations of less than the total effective amount, where the amount ultimately administered is an effective amount. Likewise, multiple administrations of an effective dose may be desirable where the second or subsequent administration is performed at a time well separated from the first administration. That is, because the cerium oxide nanoparticles are highly stable, even after being administered, repeated administrations of effective doses are envisioned as occurring at widely spaced intervals, such as months or years apart.

Furthermore, where multiple administrations are performed, different modes of administration may be used. For example, if two doses are administered, one can be an injection whereas the other can be oral. In addition, if three or more doses are administered, two or more may be by the same mode, while the remaining may be from one or more different mode, in any combination, number, and order. Of course, where multiple administrations are used, each administration may be by a different mode. The mode of administration, the number of times it is repeated, and the sequence of modes of administration may be selected by those of skill in the art based on numerous considerations, and such selection is well within the abilities of those of skill in the art.

The method can also be practiced in vitro which means that contacting at least one cell with at least one cerium oxide nanoparticle can occur in a petri dish, a test tube, an IV tube, or any other container applicable for contacting. When practiced in vitro, it may be a method for identifying parameters that are useful in in viva treatment regimens. The method can be practiced to study the effects of combinations of nanoparticles with drugs on cells. For example, the cerium oxide nanoparticles can be combined with other known antioxidants such as vitamin E, n-acetyl cysteine, or melatonin. The cerium oxide nanoparticles could also be combined with disease specific drugs. The in vitro methods can also comprise using the cerium oxide nanoparticles as a research tool to observe the effects of free radicals on cells or observe the cells for changes in protein expression, cell morphology, or any other characteristic of interest.

In preferred embodiments, the method is practiced with size-limited cerium oxide nanoparticles made by a method other than a sol-gel method. The nanoparticles useful in the present invention have pre-defined sizes clustered tightly within a range. In general, the particles have a size of about 1 nm or less to about 500 nm In embodiments, the particles are 11 nm or more. In embodiments where particles are taken into the interior of cells, the preferable range of particles that are taken into the cell are from about 11 nm to about 50 nm, such as about 20 nm. In embodiments where particles exert their effects on cells from outside of the cells, the preferable range of particles that are extracellular are from about 11 nm to about 500 nm. In embodiments, the particles are from about 40 nm to about 500 nm. In other embodiments, the particles are from about 11 nm to about 40 nm, such as from about 11 nm to about 20 nm, about 15 nm to about 20 nm, about 11 nm to about 15 nm, or about 30 nm to 40 nm. Of course, any specific size range within these general sizes can be provided, the size being selected by the practitioner based on any number of parameters. According to the invention, the term "about" is used to indicate a margin of error for a statistically significant portion of the particles of 10%. Thus, particles of a size of 20 nm include those in which a majority of the particles fall within the range of 18 nm to 22 nm. In embodiments, 95% of the cerium oxide nanoparticles have a size of between about 15 nm and about 25 nm. In embodiments, 95% of the cerium oxide nanoparticles are within 5% of 20 nm. In other embodiments, 90% of the cerium oxide nanoparticles have a size of between about 18 nm and about 22 nm.

The present invention provides methods of treating individuals suffering from, or suspected of suffering from, a disease or disorder involving free radicals, such as oxygen radicals. It likewise provides methods of treating individuals suffering from, or suspected of suffering from a complication of an injury that results from free radicals, such as oxygen radicals, or results in the production of free radicals, such as oxygen radicals. In general, the methods of the invention comprise administering to an individual (used interchangeably herein with "subject" and "patient") an amount of cerium oxide nanoparticles sufficient to reduce or eliminate cell, tissue, or organ damage in the individual that is caused by free radicals. Thus, the invention encompasses the use of cerium oxide nanoparticles in enhancement of cell and organism longevity, reduction of inflammation and inflammatory disorders, reduction in tissue damage due to inflammatory disorders, and reduction in radiation injury.

While the above disclosure discusses administration in vivo, it is important to recognize that the present invention also encompasses administering ex vivo. Thus, a method according to the invention can comprise removing at least one cell from an organism, administering cerium oxide nanoparticles to that cell, then returning the cell to its natural environment (e.g., into the body of the patient). In such situations, the act of administering can be simply exposing the nanoparticles to the cell, for example in a culture dish or a tube. In one particular embodiment, the method of ex vivo administration comprises obtaining blood from a patient, exposing the blood to cerium oxide nanoparticles, and returning the treated blood to the patient. The method can comprise separating cerium oxide nanoparticles from the blood prior to returning the blood to the patient.

In one embodiment of the method of the present invention, the cerium oxide nanoparticles allow an increase in longevity of prokaryotic cells. For example, adding the cerium oxide nanoparticles to a large scale E. coli cell culture to allow longer production of overexpressed protein may allow more efficient and cost effective production. Relevant human proteins that could be overexpressed include antibody fragments, single-domain antibodies, and any other protein important in human health, including what are presently known as "biologicals" in the pharmaceutical industry.

In another embodiment, the cerium oxide nanoparticles allow an increase in longevity of eukaryotic cells. In one example, the nanoparticles could be used to increase the longevity of yeast cell cultures that produce human proteins. Specifically, yeast cultures that produce human proteins significant in human health, such as Bacillus anthracis protective antigen, hepatitis vaccines, and malaria antigens could be grown for longer periods of time. Continuous fermentation using immobilized yeast cell bioreactor systems to produce consumable and other products, such as beer, could also benefit with increased longevity of the yeast cells after addition of cerium oxide nanoparticles. The same effect of the cerium oxide nanoparticles could be used in plant cell cultures, such as cultures producing human vaccine antigens or other human proteins. Also, mammalian cell cultures that produce recombinant &man antibodies and other important proteins for human health could benefit from increased longevity due to the addition of cerium oxide nanoparticles.

In another embodiment, the present invention is used to affect, either prophylactically or therapeutically, cell longevity in organisms. The methods treat or affect, either prophylactically or therapeutically, diseases or disorders associated with free radicals, or cell death or tissue or organ damage due to free radicals. In general, the methods comprise administering to a subject an amount of cerium oxide nanoparticles sufficient to reduce, eliminate, or block cell, tissue, or organ damage caused by free radicals in the subject.

In one embodiment, the cerium oxide nanoparticles can be taken up by the cell. In this case, they can act to reduce or eliminate free radicals within the cell. This method can be used for the prevention or treatment of brain disease, spinal cord disease, or other neurological trauma. This method can also be used for the treatment or prevention of neurodegenerative disorders such as Alzheimer's disease, Parkinson's disease, Huntington's disease, amyotrophic lateral sclerosis (ALS), multiple sclerosis, toxin-mediated damage, or stroke. This method may be used in the treatment or prevention of cardiovascular disease, diabetes, diseases of the retina, asthma, respiratory dysfunctions, and allergic or autoimmune diseases, such as chronic obstructive pulmonary disease and lupus. It is to be understood that the diseases stated above are only examples and are not to be understood as limiting the invention in anyway.

In another embodiment, the cerium oxide nanoparticles are not taken up in any significant amount by the cells, but go into intravascular or interstitial spaces. In this embodiment, the nanoparticles can act to reduce or eliminate free radicals outside the cell. This can result in reduction of inflammation and inflammatory disorders. The cerium oxide nanoparticles can reduce inflammation systemically (throughout a subject's body) or locally (at the site of the inflammatory cells). The nanoparticles can reduce or eliminate inflammation that leads to preeclampsia or inflammation caused by wounding. This can also reduce or eliminate inflammation caused by the insertion of a medical prosthesis into the subject. Nanoparticles may be retained at particular sites, at least substantially retained for periods of time, by inclusion of the nanoparticles into compositions, such as dissolvable or porous matrices and the like.

The cerium oxide nanoparticles can also contact the surface of the subject's skin and increase cell and organism longevity on the surface of the skin. Skin aging and inflammation of the skin are closely linked. In inflammation, there is an increase in neutrophil activity that involves a change in the oxidation state of the cell. Free radicals are generated which activate the chemical mediators of inflammation. In skin aging, free radicals are formed from normal metabolism, UV irradiation, and other environmental factors. The use of cerium oxide nanoparticles on the surface of the skin may prevent aging of the skin or reduce damage already inflicted on the skin. This embodiment may be used in makeup or anti-aging lotion. It may be in the form of a cream, lotion, gel, solid stick, powder or any other acceptable composition that is known in the art.

The cerium oxide nanoparticles can also be used in protection against forms of radiation, such as UV irradiation. It is known in the art that large cerium oxide molecules, as well as other oxide molecules such as zinc oxide, have the ability to protect a subject's skin from UV irradiation caused by the suds rays. However, it has not been shown until now that cerium oxide nanoparticles, which enter a cell, have protective characteristics against radiation intracellularly. The data presented here shows that cerium oxide nanoparticles can function to protect against forms of radiation such as UV and gamma radiation. The present invention provides a method for protection against other forms of radiation as well, such as beta and X-ray radiation. It is to be noted that the mode of action of the cerium particles of the present invention differs from the mode of action of larger particles in that the larger particles known in the art act to block, reflect, etc. UV light from entering cells, whereas the nanoparticles of the present invention act at a biochemical level to counteract the effects of the UV light within the cells.

Another embodiment of the invention is prophylactic radioprotection of a subject. For example, if a subject requires radiation treatment for cancer, some of the normal, healthy cells surrounding the cancerous cells will be exposed to the radiation as well. The present invention addresses this problem by providing a method for protecting the normal, healthy cells by exposure to the cerium oxide nanoparticles before radiation treatment. In, other examples, a subject can be exposed to cerium oxide nanoparticles for radioprotection in work environments with high radiation exposure or in military or bioterrorism uses.

In a further aspect, cerium oxide nanoparticles and compositions comprising cerium oxide nanoparticles are provided. The cerium oxide nanoparticles are size-limited and provided in an amount sufficient to provide one or more doses to a subject in need or suspected of being in need of, treatment for a disease or disorder involving free radicals. Compositions may comprise cerium oxide particles of the invention along with one or more other substances, which are typically substances that are biologically tolerable in that they may be exposed to living cells without killing the cells. In embodiments, the other substances are pharmaceutically acceptable substances. As used herein, "pharmaceutically acceptable substance" is intended to include solvents, coatings, antibacterial and antifungal agents, and any other ingredient that is biologically tolerable. Examples of such carriers include, but are not limited to, water, saline, dextrose solution, human serum albumin, liposomes, and hydrogels. The use of such media and agents for pharmaceutically active substances is well known in the art, and thus further examples and methods of incorporating each into compositions at effective levels need not be discussed here.

Certain aspects of the invention provide for the use of cerium oxide nanoparticles in the treatment of diseases and disorders associated with free radicals, such as oxygen free radicals. The use is in particular for in vivo therapeutic or prophylactic methods of protecting cells from free radical damage. Certain other aspects of the invention provide for the use of cerium oxide nanoparticles in the preparation of compositions for medical use, such as pharmaceutical or therapeutic compositions. In general, use of the particles is in combining them with other substances to make medicinal compositions.

Another aspect of the invention provides a container containing cerium oxide nanoparticles. In general, a container according to the invention contains a sufficient amount of size-limited cerium oxide nanoparticles made by a method other than a sol-gel method to provide at least one dose of cerium oxide to a subject suffering from, or at risk of suffering from, a disease or disorder involving free radicals, such as oxygen radicals. For example, the container may contain sufficient cerium oxide nanoparticles and, optionally, one or more other biologically tolerable substance, for one dose to a human or non-human animal subject. In certain embodiments, the container is provided in a package with one or more other containers and/or with one or more articles of manufacture or devices having use in delivery of substances to subjects (e.g., syringes, needles, antiseptic swabs, sterile saline solution). In some embodiments, kits comprising one or more containers are provided.

Regardless of whether provided alone, as part of a composition, or as part of a kit, the cerium oxide nanoparticles may be provided in any suitable physical form. Thus, they may be provided as dry particles or as part of a liquid composition. When part of a liquid composition, the composition typically will comprise water or an aqueous buffer, such as phosphate buffered saline (PBS) or other salt buffers. In general, it is preferred that the liquid composition be suitable for introduction into a living organism or for contact with a living cell without causing deleterious effects, such as cell toxicity. It is to be understood that this general preference permits inclusion of toxic components in the liquid composition as long as those components, when exposed to a living cell upon exposure to the cell, are present in a non-toxic form or at non-toxic levels. In embodiments where dry nanoparticles are administered, the nanoparticles may be in a purified state or may be in a composition comprising one or more other component. It is preferred that the other component(s) be non-toxic or, if toxic, present in an amount that, when administered, is not toxic to the cell or subject as a whole. Examples of non-toxic components include, but are not limited to, salts (e.g., sodium salts such as sodium phosphate or sodium chloride); sugars (e.g., glucose, sucrose); preservatives; and antibiotics, anti-inflammatories, albumin, lipids, or other drugs. The vehicle of delivery may be in the form of an oral solution, gel, tablet, capsule, powder, suppository, infusible, losenge, cream, salve, inhalant, or injection.

Typically, the particles or composition comprising the particles will be sterile or will have been sterilized prior to administration to a subject or other use. The particles may be sterilized using any suitable technique known in the art, including, but not limited to, heat sterilization, filtration, and irradiation. Thus, in embodiments, the method of the invention further comprises providing sterile or sterilized cerium oxide nanoparticles, or further comprises sterilizing the nanoparticles prior to administering them to a subject.

The invention provides compositions comprising cerium oxide nanoparticles. The compositions can comprise a pharmaceutically suitable carrier, a nutritional supplement, or a dietary supplement. While not being so limited, typically the compositions comprise one or more other substances other than the nanoparticles, where the other substances are biologically tolerable (i.e., non-toxic or present in an amount that is non-toxic). Examples of such substances are well known to those of skill in the art and include, without limitation, sugars, salts, lipids, drugs, excipients, carriers, flavorants, fillers, binders, gums, colorants, water, buffers, detergents, biologically active compounds, and the like.

The present invention also provides kits. In general, the kits comprise cerium oxide nanoparticles in an amount sufficient to treat at least one patient at least one time to reduce or eliminate free radicals that can cause cell, tissue, or organ damage. Typically, the nanoparticles of the kit will be supplied in one or more container, each container containing a sufficient amount of nanoparticles for at least one dosing of the patient. The kits can comprise other components, such as some or all of the components necessary to practice a method of the invention. For example, in embodiments of the kit, albumin is included, either as a separate component or as part of a composition comprising the nanoparticles. The albumin is provided to lessen the amount or use of disruption of the nanoparticles, for example by sonication at 5-20 Hz for 2 minutes, that can sometimes be needed to provide certain formulations for delivery. The kits may contain a syringe for administering a dose of the nanoparticles. The kits may also comprise filters for sterilization of the particles prior to delivery; however, it is preferred that the particles be sterilized prior to packaging in the kits, or the entire kit be sterilized after all components are packaged. It may likewise contain sterile water or buffer for rehydration or reconstitution of dry nanoparticles, prior to administration of the particles to a patient. In embodiments, multiple doses of nanoparticles are provided in the kit, either all in a single container (e.g., a vial) or distributed among two or more containers. As the invention contemplates administering or delivering (used synonymously herein) of nanoparticles m liposomes, kits according to the invention may comprise liposomes, particularly liposomes loaded with the nanoparticles.

EXAMPLES

The invention will be further explained by the following Examples, which are intended to be purely exemplary of the invention, and should not be considered as limiting the invention in any way.

Example 1

Extension of Cell and Organism Longevity

A single 10 nM dose of cerium oxide nanoparticles extended the life span of cultured rat brain cells (neurons, astrocytes, microglia) from 28 to 182 days (6 months). For delivery, the nanoparticles were in a non-agglomerated form. To accomplish this, stock solutions of about 10% by weight were sonicated in ultra-high purity water (16 megaohms) or in normal saline prepared with ultra high purity water. Stocks were sonicated with a probe sonicator for 3 minutes. Dilutions were made, beginning with 10 mM, down to 100 nM or lower. No phosphate or other ionic buffers were used because these were found to increase agglomeration. All serial dilutions were sonicated for 3 minutes prior to use or to further dilution. Importantly, aged neurons and astrocytes were functionally equivalent to their younger, untreated, counterparts. Neurotransmission in response to glutamate, GABA, and acetylcholine in cerium oxide nanoparticle-treated aged cultures was similar to younger, cultured controls. Further, similar doses of cerium oxide nanoparticles administered orally (in the food) extended the lifespan of the fruit fly, *Drosophila melanogaster*.

Figure 2:
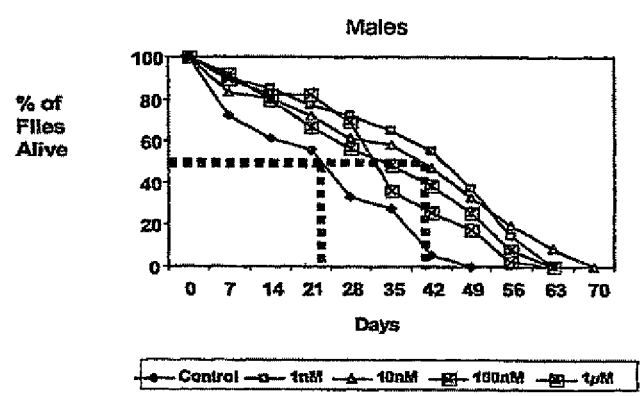
FIG. 2 depicts the effects of cerium oxide nanoparticles on the lifespan of *D. melanogaster* flies.

FIG. 1 depicts the results of experiments to determine the effect of nanoparticles on the maximum lifespan of organotypic brain cells in culture. The mixed brain cell cultures from rat cerebral cortex were treated with 10 nM cerium oxide nanoparticles on day 10 in vitro. Controls received vehicle alone (normal saline). The figure shows that the nanoparticles has a dramatic effect on cell lifespan. DIV=Days In Vitro FIG. 2 depicts the results of experiments to determine the effect of nanoparticles on the lifespan of *Drosophila melanogaster*. The results show that the lifespan of the flies is significantly increased. *Drosophila melanogaster* (Oregon R strain) were fed from eclosure with standard mix fly food with or without cerium oxide nanoparticles at the indicated concentrations. Note that not only is the maximum lifespan increased, but the time to 50% population death in increased in nanoparticle-treated vs. controls (dotted lines). Flies were fed food containing the indicated concentration of cerium oxide nanoparticles, from ecolsure throughout the lifetime. Stock concentrations of cerium oxide nanoparticles were prepared as described above (sonication methods) and added to the fly food (Jazz Mix) during preparation (i.e., while the fly food remained in liquid form). Food was sonicated 5 min after addition of particles, to ensure non-agglomerated suspension of nanoparticles in the food medium. Flies were growth under standard conditions, in vials containing 5 ml food medium and 20 flies per vial. Dead flies were counted every 1-2 days.

Example 2

Free Radical Scavenging Capacity of Cerium Oxide Nanoparticles

Given the structure of cerium oxide nanoparticles, we hypothesized that cerium oxide nanoparticles promoted cell longevity by acting as free radical scavengers. To test this hypothesis, we exposed cultured brain cells to lethal and sub-lethal doses of the free radical generating agents, hydrogen peroxide, and UV light. Exposure to cerium oxide nanoparticles afforded significant protection against both of these free radical generating agents, and reduced cell death in excess of 60%. Protection against UV and hydrogen peroxide-mediated injury was preserved in 3 month old cultures that had been treated with cerium oxide nanoparticles on day 10 in culture. Thus, the effects of cerium oxide nanoparticles are long-lasting, following a single dose.

Studies comparing the effects of cerium oxide nanoparticles to the traditional free radical scavengers Vitamin E, melatonin, and N-acetyl-cysteine demonstrated that only cerium oxide nanoparticles were capable of enhancing longevity. Further, cerium oxide nanoparticles provided superior protection to free radical mediated injury, as compared to single and multiple doses of traditional free radical scavengers.

To further confirm our hypothesis that cerium oxide nanoparticles act via a free radical scavenging mechanism, we have detected a novel shift in the excitation spectra of cerium oxide nanoparticle solutions and in cells loaded with cerium oxide nanoparticles, during free radical challenge. In cells and in cerium oxide nanoparticle solutions, excitation scans reveal a peak excitation of 451 for cerium oxide nanoparticles in the reduced (+4) valence state. Upon free radical challenge, the excitation maxima shifts to 356 nm, suggesting a change in cerium to the +3 valence state. After 5-20 minutes, the excitation spectra returns to the normal resting state, with a peak maxima of 451 excitation, suggesting regeneration of the original cerium oxide lattice structure.

Figure 3:
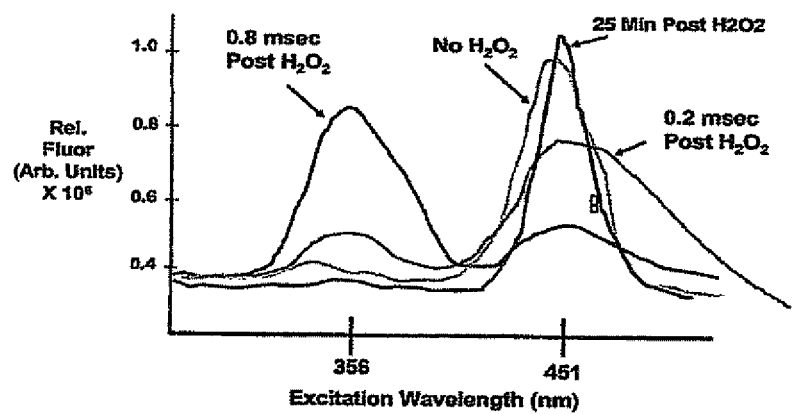
FIG. 3 depicts the excitation spectra for intracellular cerium oxide nanoparticles during a free radical scavenging event.

FIG. 3 depicts the excitation spectra for intracellular cerium oxide nanoparticles, and shows that the spectra is altered during a free radical scavenging event. For the experiments depicted in the figure, astrocytes were treated with 10 nM cerium oxide nanoparticles on day 10 in vitro, and examined fluorimetrically on day 18. Cell cultures were washed, placed in phosphate buffered saline, and subjected to excitation spectra scan as shown. Emission was measured above 510 nm. Excitation scans were collected every 0.01 msec using a high speed DeltaRam Scanner, during the addition of 100 uM $H_2O_2$ as a free radical-generating agent. Controls (untreated) cells revealed no fluorescence emission in the range and magnitude shown. The shift in excitation spectra of cerium indicates an electron shuffling event in the oxide lattice or cerium atom, as shown in FIG. 3. These results demonstrate that a similar shift in excitation spectra occurs in cells containing cerium oxide nanoparticles, which occurs during a reaction with a free radical, such as that generated by $H_2O_2$. Importantly, the return to 456 nm excitation maxima suggests that the cerium oxide nanoparticle can regenerate its free radical scavenging capacity while in the cell.

Example 3

Toxicity and Biodistribution

Using electron microscopy, microspectrophotometry, and inductively coupled plasma mass spectrometry, we found that cerium oxide nanoparticles of size less than 20 inn readily enter cultured cells and cells of living organisms. Further, doses as high as 100-fold of that which extend cell culture lifespan exhibited no overt toxicity in *Drosophila*. A single tail vein injection of 0.3-3 mM in the mouse produced no overt organ or behavioral abnormalities. Cerium oxide nanoparticles were found to accumulate preferentially in brain, heart, and lung with little excretion over a 6 month time period. At the 0.3 mM dose, tissue cerium levels approximately doubled (as compared to background), but remained in the parts per billion range.

Figure 4:
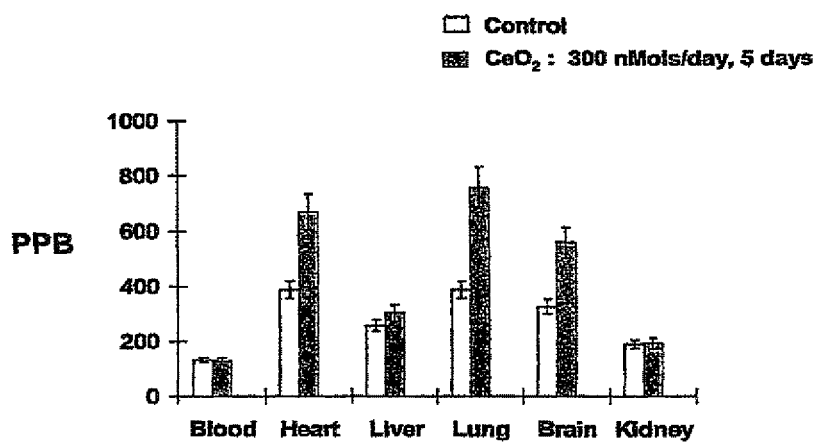
FIG. 4 depicts a drug distribution graph of tissue cerium content of BALB/c mice after injection with nanoparticles, as assayed by inductively coupled plasma mass spectrometry.

FIG. 4 depicts the results of tissue cerium measurements of mice treated with nanoparticles. More specifically, Balb/c mice were administered 5-10 ul tail vein injections each containing 300 nmoles cerium oxide nanoparticles. After 3 months, mice were euthanized and organs were harvested. Tissue cerium was measured by inductively coupled plasma mass spectrometry. It is interesting to note that the highest increases in tissue cerium concentration occurred in brain, heart, and lung, the most oxidative organs in the body.

Example 4

Protection Against Trauma

Using an in vitro model representative of human head injury that has been extensively published, we have demonstrated that brain cell injury in response to trauma may be related, in part, to generation of free radicals induced by injury. Brain cell cultures treated with cerium oxide nanoparticles on day 10 in vitro showed a 60-70% reduction in cell injury when trauma was administered on days 15-18 in vitro. Further, delivery of cerium oxide nanoparticles up to 3 hrs post-injury reduced neuronal death by 40-50%, depending on the degree of injury. Thus, cerium oxide nanoparticles represent a treatment for trauma, and other forms of neurodegeneration associated with free radical injury.

In brain trauma, neuronal dysfunction often manifests, causing persistent neurological deficits. Here, we demonstrate this correlates to human head injury with an in vitro model. We found that pre- or post-injury delivery of nanoparticles significantly reduced neuronal dysfunction, as measured by neurotransmitter-stimulated calcium signaling, in both astrocytes and neurons.

Figure 5:
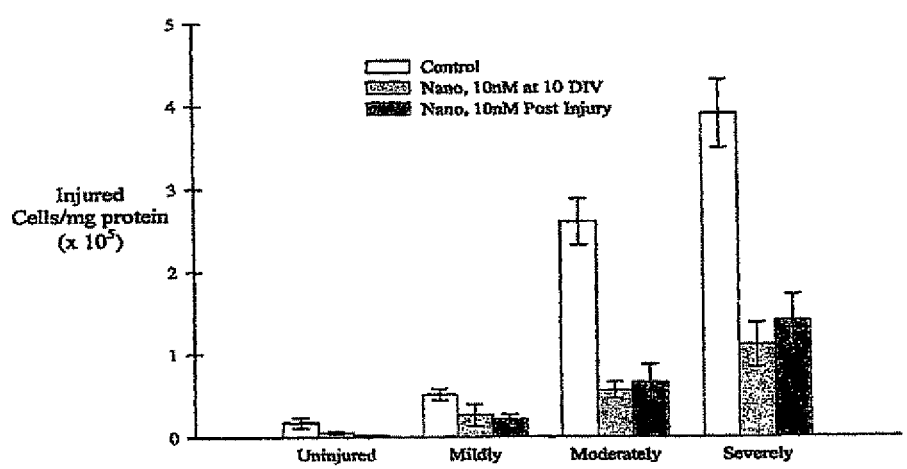
FIG. 5 shows the response of brain cell cultures (neuronal death) treated with nanoparticles, as assessed by propidium iodide staining.

FIG. 5 shows the effect of nanoparticles on brain cells subjected to trauma. Mixed organotypic brain cell cultures were subjected to in vitro trauma as previously described (Zhang, Rzigalinski, et al. Science 274: 1921-1923, 1997). Cerium oxide nanoparticles (10 nM) were delivered to the cultures either on day 10 in vitro or 3 hours post injury and neuronal death was assessed by propidium iodide staining at 24 hrs post injury. The positive effects on cells is evident.

Figure 6:
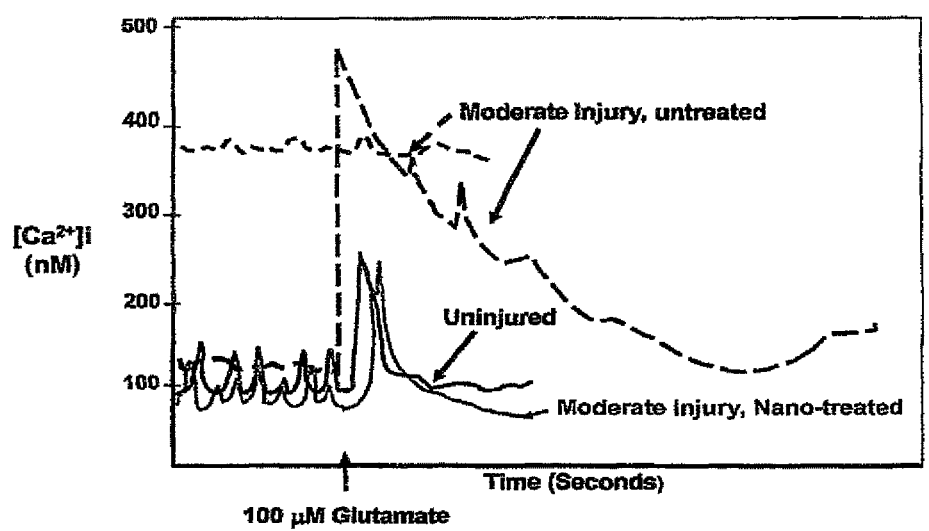
FIG. 6 shows the response of brain cell cultures (neuronal death) treated with nanoparticles.

FIG. 6 further shows the effect of nanoparticles on brain cells subjected to trauma. Mixed organotypic brain cells were subjected to in vitro trauma as described above. Cerium oxide (10 nM) nanoparticles were delivered 3 hrs post injury and neuronal intracellular free calcium ($[Ca^{2+}]_i$) signaling was determined at 24 hrs post injury using Fura-2 microspectrophotometry. Uninjured neurons (solid black line) showed regular intracellular free calcium oscillations, indicative of robust inter-neuronal signaling. Glutamate induced a rise in $[Ca^{2+}]_i$ to 262 nM, followed by a return to basal. In injured, untreated cultures (dashed line) $[Ca^{2+}]_i$ signaling is perturbed. Neurons either had dramatically elevated basal $[Ca^{2+}]_i$ with no response to glutamate, or a dramatically enhanced response to glutamate, suggestive of excitotoxicity. In injured cultures treated with cerium oxide nanoparticles, normal basal $[Ca^{2+}]_i$, oscillations and glutamate signaling were preserved (lt gray line). Results shown are representative of 12 separate experiments including over 90 neurons.

Example 5

Anti-Inflammatory Properties of Nanoparticles

Free radical production and the associated cell damage are components of many inflammatory disorders, including arthritis, Alzheimer's Disease, multiple sclerosis, atherosclerosis, ALS, Parkinson's disease, autoimmune diseases, and allergic disorders. We found cerium oxide nanoparticles to be potent inhibitors of inflammation and inflammatory cell damage. Our studies indicate that cerium oxide nanoparticles reduce the inflammatory response in brain microglia (MG), reduce neuronal death induced by activated, inflammatory brain MG, as well as reduce the release of interleukin 1-β and inflammatory mediators of the arachidonic acid cascade in brain MG. We also found that cerium oxide nanoparticles reduce the inflammatory activation state of human neutrophil and macrophage like cells lines, HL-60 and U937 and reduce the inflammatory response initiated by histamine, bacterial lipopolysaccharide (LPS), and fMLP (f-met-leu-phe, chemotactic peptide) in human neutrophil and macrophage-Re cell lines (HL-60 & U937). Therefore, cerium oxide nanoparticles represent a novel treatment for inflammatory and immune disorders.

Figure 7:
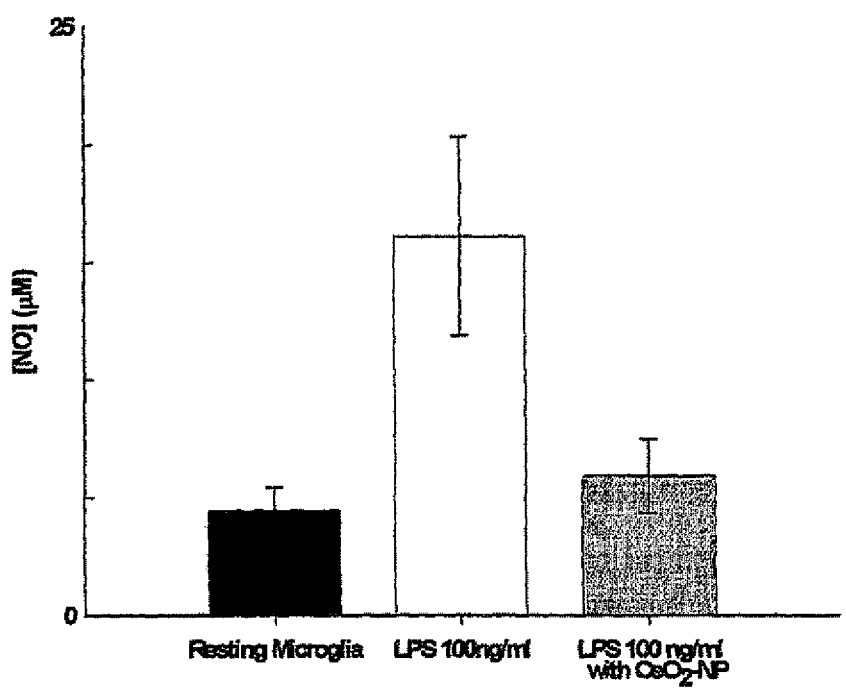
FIG. 7 demonstrates the response of brain cell cultures treated with nanoparticles in terms of nitric oxide release.

FIG. 7 shows that cerium oxide nanoparticles reduce the inflammatory response initiated by lipopolysaccharide (LPS). Experiments have shown that microglia (MG), as inflammatory cells, respond to traumatic brain injury by up-regulation of inflammatory functions, known as "activation". Once "activated", MG become essential in the removal of damaged or malfunctioning neurons. MG are hypothesized to exert a destructive force on healthy, bystander neurons due to prolific release of free radicals, which damage surrounding neurons. Our previous studies have shown that neuronal death is reduced in traumatically injured organotypic brain cell cultures by treatment with cerium oxide nanoparticles, a potent free-radical scavenger. One of the free-radicals released by MG when subjected to injury is Nitric Oxide (NO). MG were treated once with 10 nM $CeO_2$-NP for 24 hrs, to allow uptake of nanoparticles. After washing and changing the media, MG were treated with 100 ng/ml LPS to induce the inflammatory response. Morphology and release of NO were examined. MG exposed to 100 ng/ml LPS for 24 hours exhibited release of NO of 16.1 mM. When treated with 10 nM $CeO_2$-NP for 24 hours prior to exposure, NO release decreased by 62.0%, demonstrating that $CeO_2$-NP does decrease release of inflammatory mediators that may enhance neuronal death.

Figure 8:
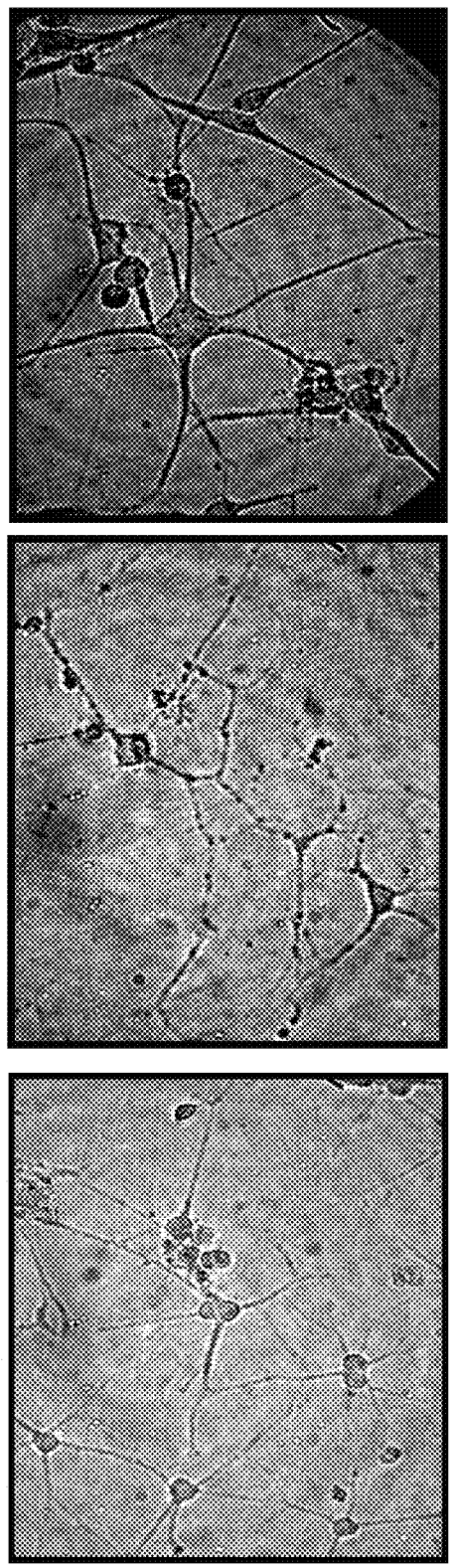
FIG. 8 shows the morphological effect of cerium oxide nanoparticles on brain microglia.

As shown in FIG. 8A, resting MG have compact cell bodies with long, branched processes. In FIG. 8B, MG were stimulated with LPS. Note the dramatic morphological changes as compared to the resting state (8A). LPS-induced morphological changes are blocked by $CeO_2$-NP as shown in 8C.

Example 6

Radioprotective Effects of Nanoparticles

Radiation injury induces cell death by free radical-mediated damage to cellular DNA, RNA, and proteins. Cerium oxide nanoparticles reduced brain cell death associated with 1, 3, and 5 Gray by 78, 62, and 48%, respectively. In these experiments, a single 10 nM dose of nanoparticles was administered on day 10 in vitro, with irradiation of cultures on day 12-15. Further, a reduction in injury was observed even when particles were administered up to 3 hrs post irradiation. These results suggest that cerium oxide nanoparticles have significant radioprotective properties, and may be utilized in radiation protection for military and anti-bioterrorism applications. Additionally, nanoparticles have the potential for use in cancer therapy, by protection of non-cancerous "bystander" cells from radiation injury.

Figure 9:
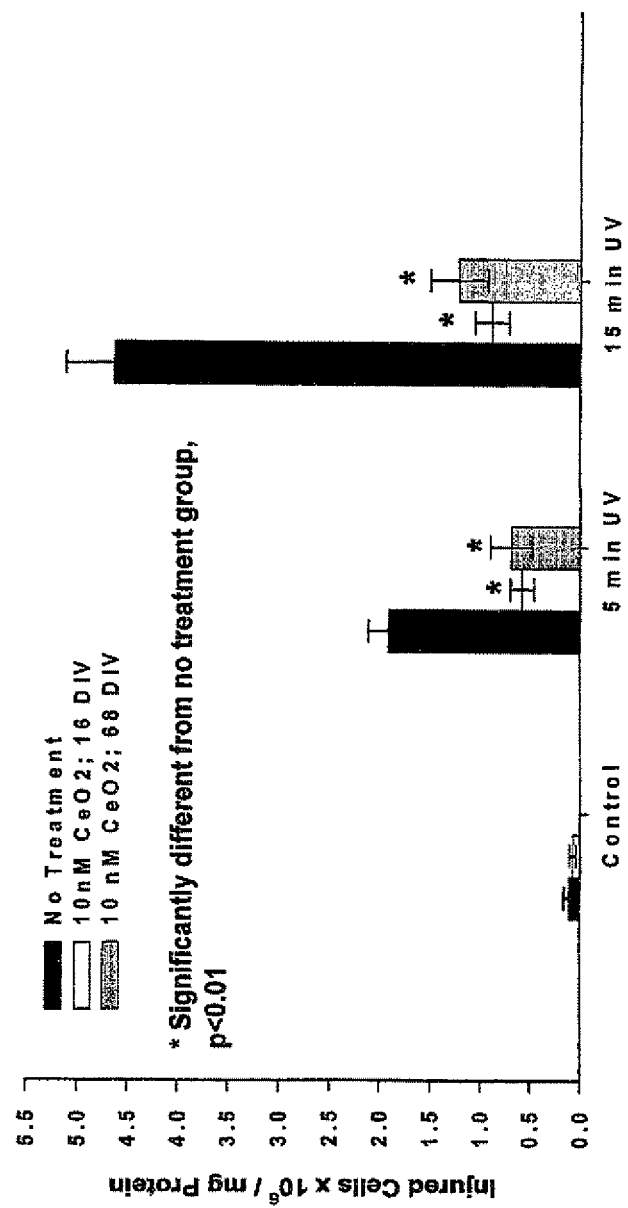
FIG. 9 shows the effect of pretreatment with cerium oxide nanoparticles on exposure to UV radiation.
Figure 10:
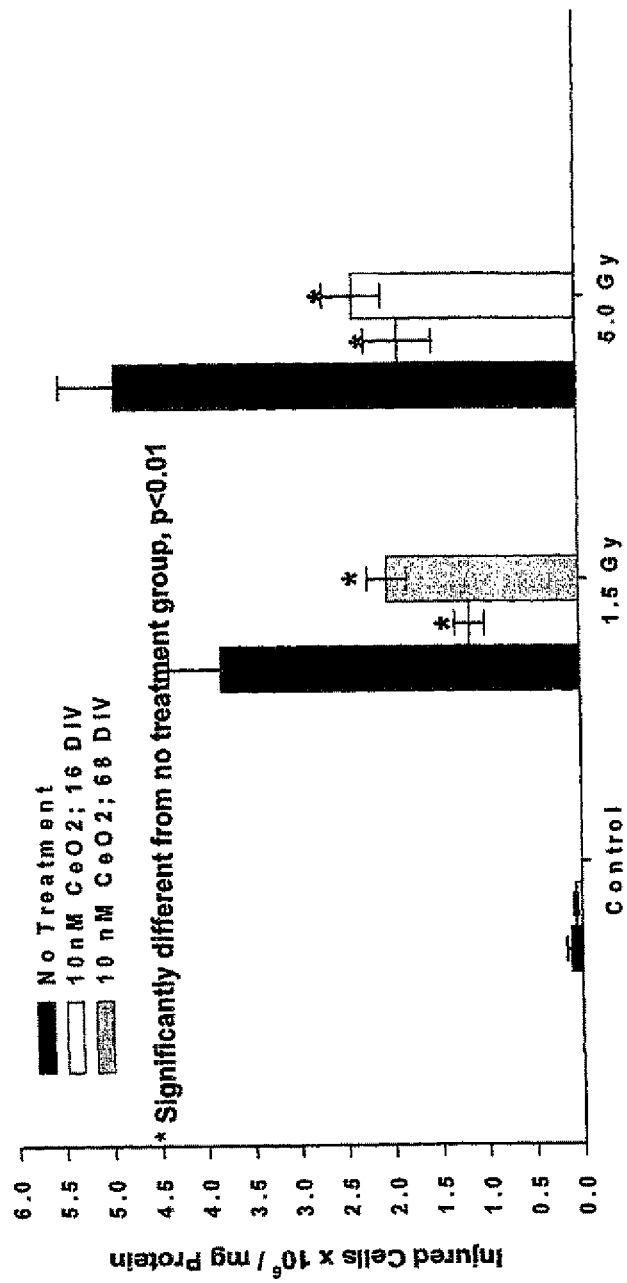
FIG. 10 demonstrates the effect of pretreatment with cerium oxide nanoparticles on exposure to gamma-irradiation.

FIGS. 9 and 10 show the effect of pretreatment with cerium oxide nanoparticles on exposure to radiation. Mixed organotypic rat brain cells were obtained from neonatal rat pups and cultures as previously described (Zhang et al., Science, 274, 1921-1923, 1996.). Cultures were treated+10 nM $CeO_2$-NP on day 10 in vitro, by delivery to the tissue culture medium for 24 hrs, followed by regular medium replacements. After 14-16 DIV, free radical damage was assessed by exposure to ultraviolet light for increments of 5 minutes or 15 minutes, followed by measurement of cell death with Propidium Iodide (PrI). For gamma-irradiation studies, cells were exposed to 1.5 or 5 Gray radiation for 1 minute. Additionally, aged cultures (68 DIV) treated with $CeO_2$-NP were also exposed to UV and gamma-irradiation, to determine whether the protective effects of $CeO_2$-NP were maintained in aged cultures.

For the experiments in FIG. 9, mixed brain cell cultures were treated with $CeO_2$-NP at 10 DIV, and exposed to UV light at 16 or 68 DIV. Note that there are no 68 DIV untreated controls, since untreated mixed brain cell cultures do not survive this long. $CeO_2$-NP treatment dramatically increased survival after 5 and 15 min UV exposure, which are known to induce cell death through free radical production. Further, the protective effects of a single 10 nM dose of $CeO_2$-NP were maintained through the extended lifespan of these cells.

For the experiments in FIG. 10, mixed brain cell cultures were exposed to a second source of free radical generation, gamma-irradiation. Cultures were treated with $CeO_2$-NP and exposed to irradiation as described above. A single 10 nM dose of $CeO_2$-NP delivered at 10 DIV provided significant protection against gamma-irradiation, which was again maintained through the extended lifespan of the cultures.

Figure 11:
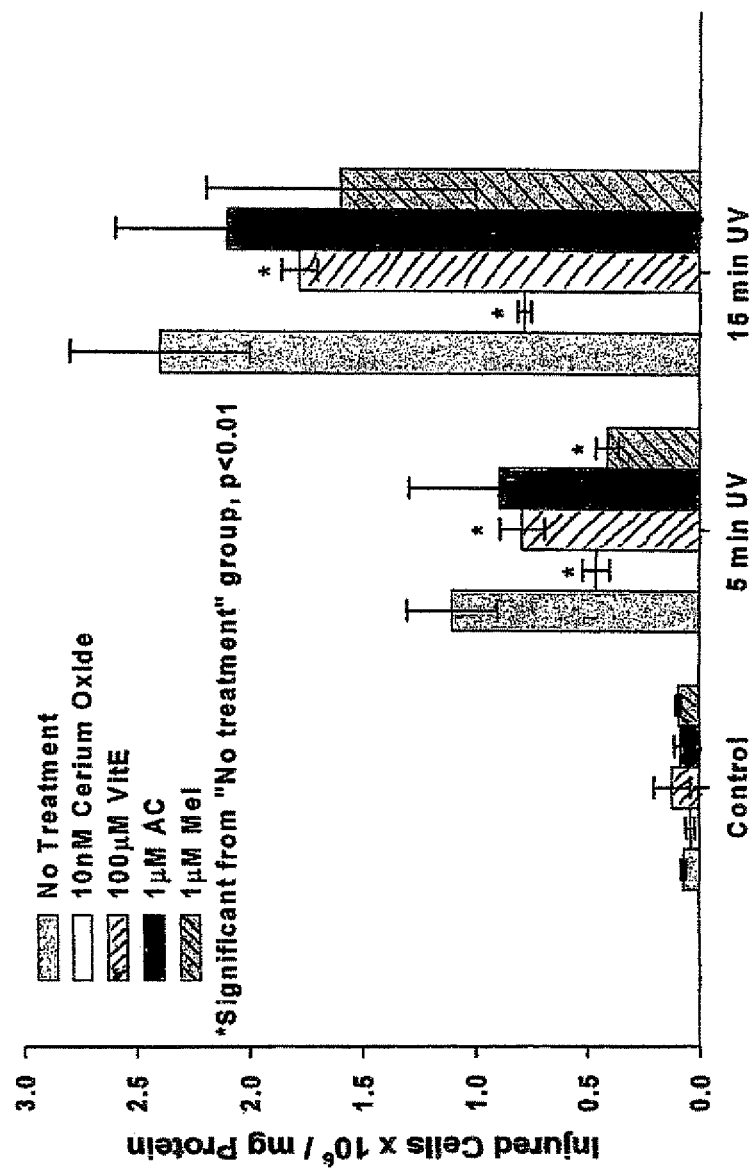
FIG. 11 shows the effect of pretreatment of a single dose of cerium oxide nanoparticles against free radical mediated injury as compared to a single dose of Vitamin E, n-Acetyl Cysteine, or Melatonin.
Figure 12:
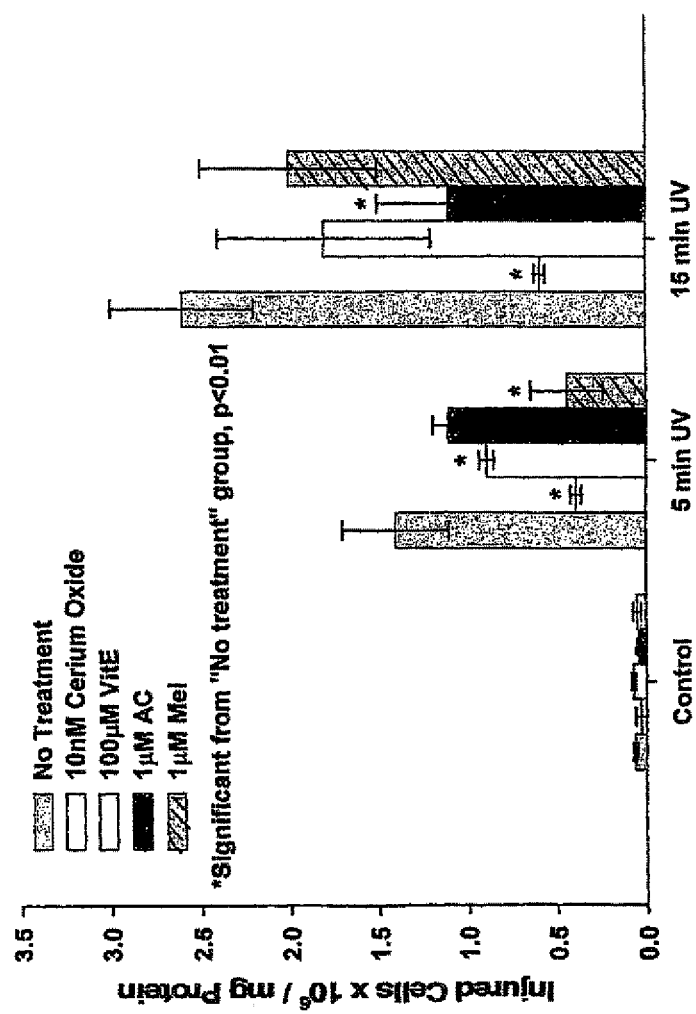
FIG. 12 shows the effect of pretreatment of a single dose of cerium oxide nanoparticles against free radical mediated injury as compared to multiple doses of Vitamin E, n-Acetyl Cysteine, or Melatonin.

FIGS. 11 and 12 show that cerium oxide nanoparticles provide greater protection against free radical mediated injury as compared to single or multiple doses of Vitamin E, n-Acetyl Cysteine, or Melatonin. In these experiments, cells were cultured in 6-well plates. Three wells were used as controls while the other three were treated with one of the following agents at 10-DIV: 10 nM Cerium Oxide nanoparticles, 100 mM Vitamin. E, 1 mM n-Acetyl Cysteine, or 1 mM Melatonin. Drugs were delivered directly into the tissue culture media and remained in the media for 24 hrs, followed by media replacement. Nanoparticles were only delivered once, at 10 DIV. Other agents were delivered in single or multiple doses as indicated. After 14-16 DIV, free radical damage was assessed by exposure to ultraviolet light for increments of 5 minutes or 15 minutes, followed by measurement of cell death with Propidium Iodide (PrI).

In the FIG. 11 experiments, cerium oxide nanoparticles or other free radical scavengers were delivered to the tissue culture medium on DIV 10. Medium was replaced 48 hrs later, followed by regular medium changes every 2-3 days. UV exposure was performed on DIV 14. Cerium Oxide nanoparticles reduced UV-light induced cell death 24 hr after a 5 or 15 min. exposure, by 58%. MEL reduced cell death associated with short term (5 min) UV exposure to a similar extent, but was less effective after a long term (15 min) exposure. Vitamin E afforded a modest degree of protection.

In the FIG. 12 experiments, a single 10 nM dose of cerium oxide nanoparticles delivered on DIV 10 was compared to multiple doses of other antioxidants. Vitamin E, n-Acetyl Cysteine, and Melatonin were administered at DIV 10 and again on DIV 12. Cerium Oxide nanoparticles were more efficient at decreasing UV-mediated cell injury than multiple doses of Vitamin E, n-Acetyl Cysteine, or Melatonin.

Example 7

Further Experiments on Extension of Cell and Organism Longevity

Figure 13:
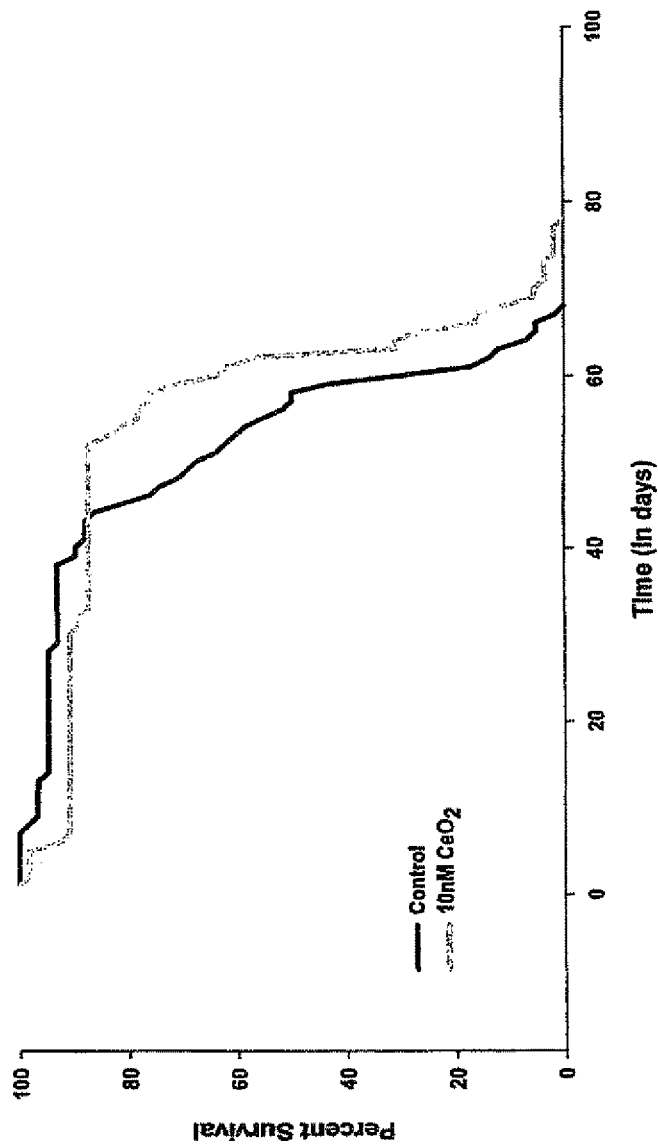
FIG. 13 shows the change in female *Drosophila* life spans when cerium oxide nanoparticles are given to the flies.
Figure 14:
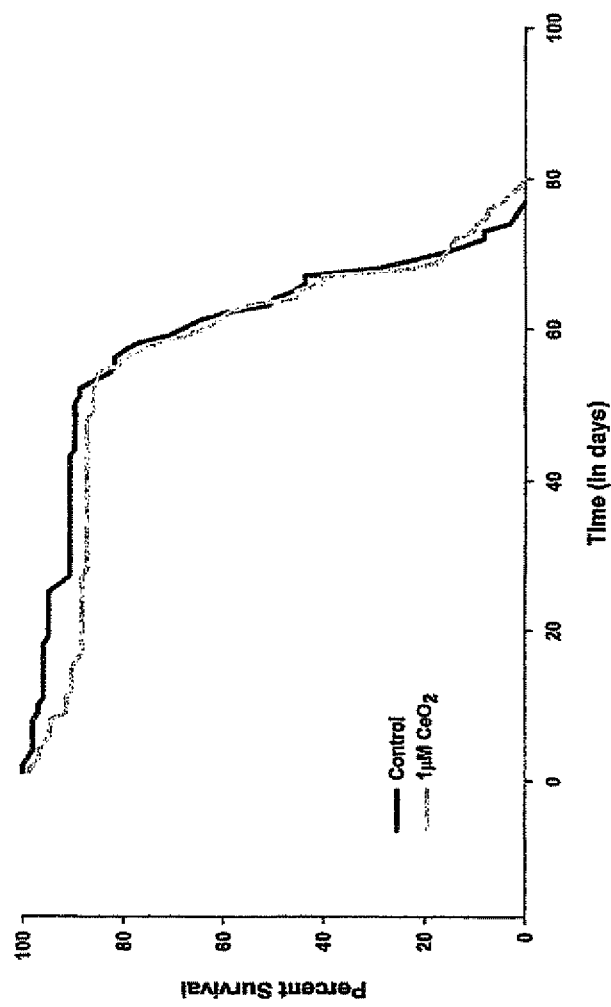
FIG. 14 demonstrates the change in male *Drosophila* life spans when cerium oxide nanoparticles are given to the flies.

FIGS. 13 and 14 show that both male and female *Drosophila* life spans are increased when cerium oxide nanoparticles are given to the flies. These longevity studies were performed by adding 10 nM $CeO_2$-NP directly to the fly food. To determine the effect of $CeO_2$-NP on survival after free radical challenge, male and female flies were cultured continuously from the day of eclosure on fly food containing 10 nM CeO2-NP. On day 35, flies were exposed to filter paper saturated with 20 mM paraquat in 5% sucrose solution for 24 hrs. Paraquat is a redox cycling pesticide known to induce fly death via free radical production. Dead flies were counted at regular intervals. Flies surviving in excess of 24 hrs were placed back into vials containing control food or food treated with the appropriate $CeO_2$-NP concentrations. Surviving flies continued to be monitored on a daily basis. Similar results were obtained in vitro with cell cultures in which 1 nM, 10 nM, and 1 uM cerium oxide nanoparticles protected the cells against death in the presence of 0.1 mM, 0.5 mM and 1 mM paraquat (data not shown).

Figure 15:
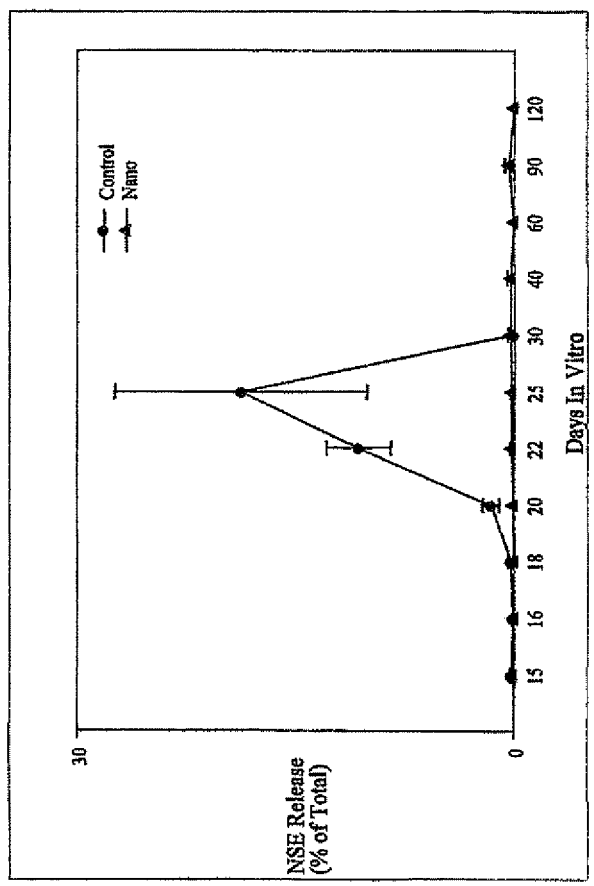
FIG. 15 shows the amount of neuron specific enolase (NSE) in tissue culture medium.

FIG. 15 shows the amount of neuron specific enolase (NSE) in tissue culture. As neurons die off in a culture, they release a characteristic enzyme, NSE. This experiment shows the amount of NSE in the tissue culture medium, as a percentage of the total left in the cultures. NSE release increases dramatically in the medium over days 20-26, as the neurons die and lyse. At day 30, all the neurons are dead. In the cerium oxide treated group (triangles), the NSE in the medium does not rise, but stays at basal levels, denoting that all the neurons are still alive.

Figure 16:
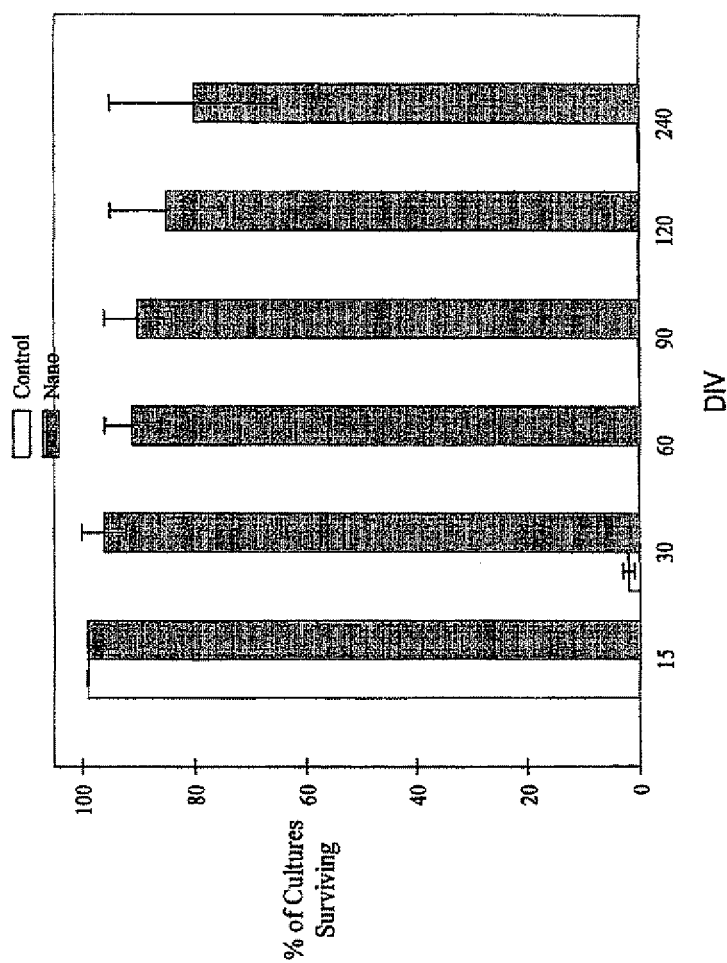
FIG. 16 shows the effect of cerium oxide nanoparticles on the longevity of tissue cultures.
Figure 17:
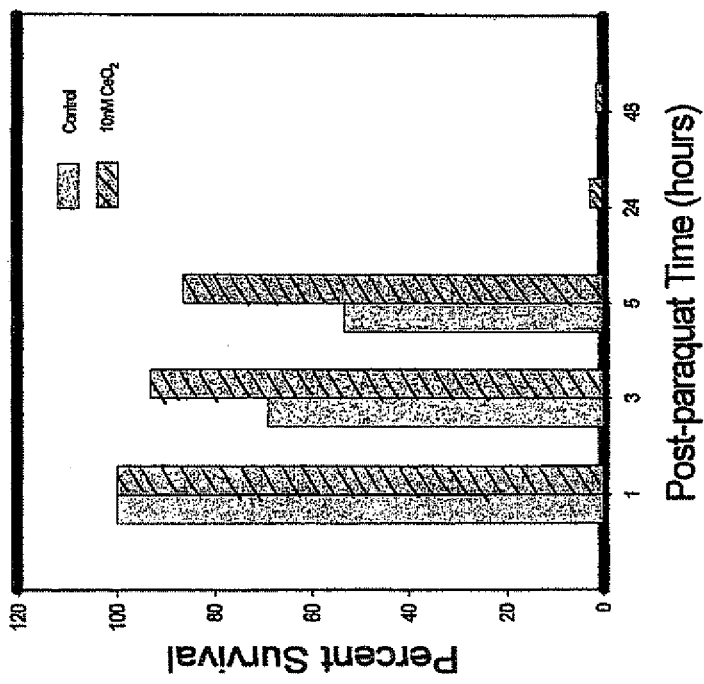
FIG. 17 demonstrates the effect of paraquat on female *Drosophila* fed 10 nM cerium oxide nanoparticles.
Figure 18:
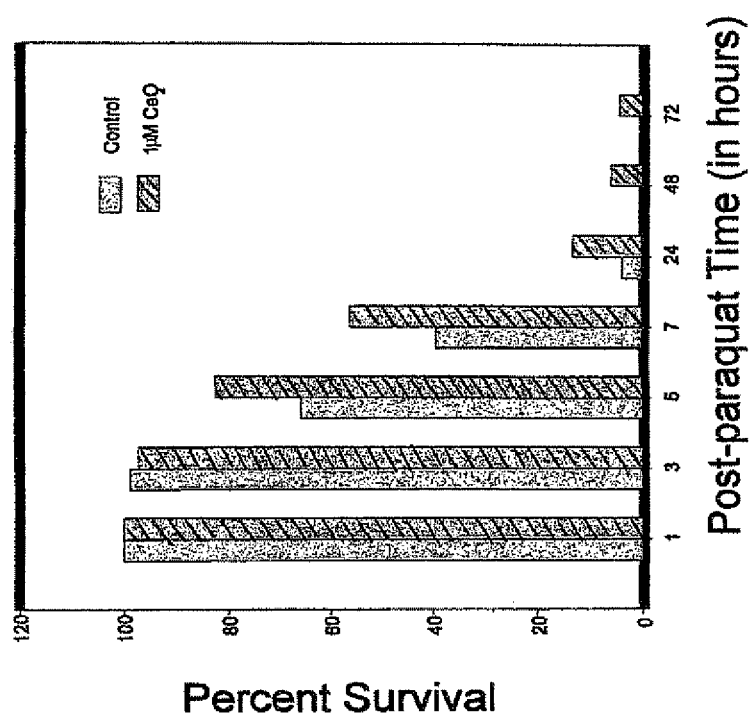
FIG. 18 demonstrates the effect of paraquat on female *Drosophila* fed 1 uM cerium oxide nanoparticles.
Figure 19:
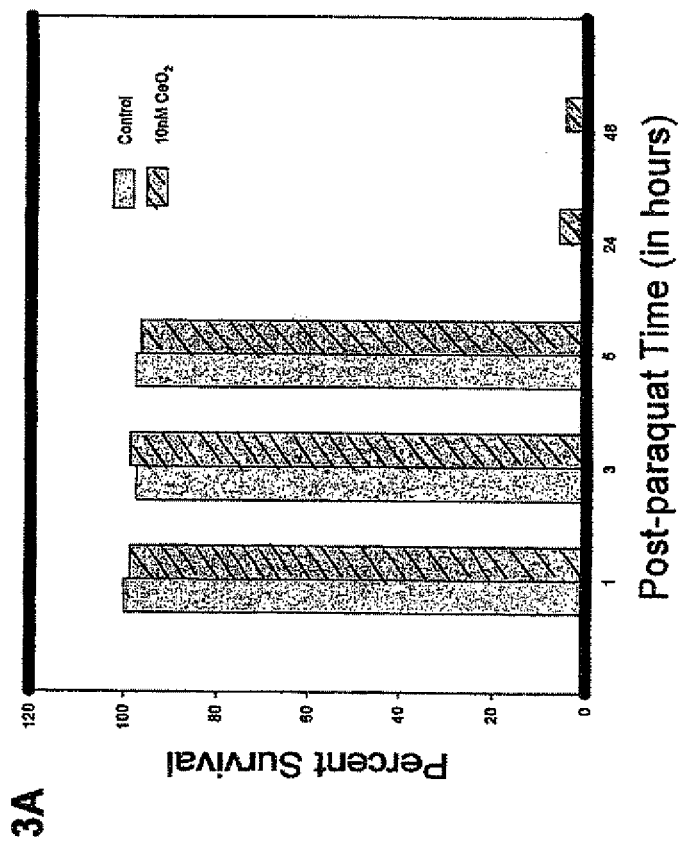
FIG. 19 demonstrates the effect of paraquat on male *Drosophila* fed 10 nM cerium oxide nanoparticles.
Figure 20:
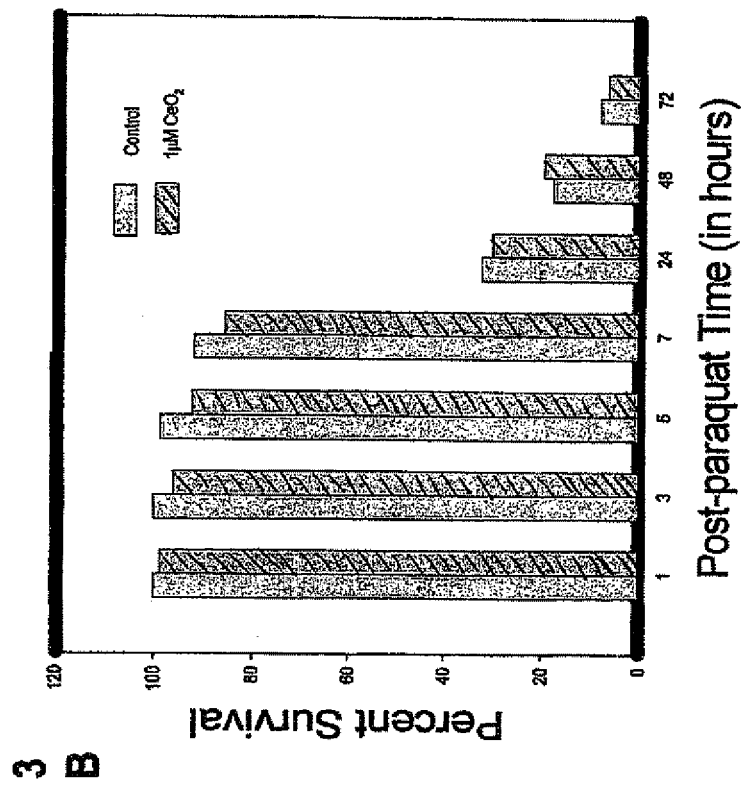
FIG. 20 demonstrates the effect of paraquat on male *Drosophila* fed 1 uM cerium oxide nanoparticles.

FIG. 16 shows the percentage of tissue cultures surviving with robust neurons and astrocytes. This experiment summarizes data for over 75 control and cerium oxide-treated cultures. Each culture was treated with a single dose of 10 nM cerium oxide nanoparticles on day 10 in vitro. This experiment demonstrates that cerium oxide nanoparticles increase the longevity of the cultures.

FIGS. 17 through 20 show that 10 nM cerium oxide nanoparticles significantly extend the average and maximum lifespan of male and female *Drosophila* when the fruit flies are introduced to paraquat, an oxidative stress inducer. In this experiment we tested the hypothesis that cerium oxide nanoparticles act as free radical scavengers in *Drosophila melanogaster*. To induce oxidative stress, we used paraquat (methyl viologen). The literature reports that paraquat induces severe oxidative stress in the fruit fly, via production of superoxide ions, with an LD50 of 10 mM. Hence, paraquat is routinely used to test effects of various biochemical agents on reduction of oxidative stress, via examining survival after paraquat challenge. In this study, 100 male and female flies were cultured continuously from the day of eclosure on fly food containing 10 nM and 1 uM cerium oxide. On day 35, flies were deprived of food for three hours, then exposed to filter paper saturated with 20 mM paraquat in 5% sucrose solution for 24 hours. Dead flies were counted at regular intervals. Flies surviving in excess of 24 hrs were placed back into vials containing control food or food treated with the appropriate nanoparticle concentrations. Surviving flies continued to be monitored on a daily basis.

Example 8

Further Experiments Showing the Protection Against Trauma

Figure 21:
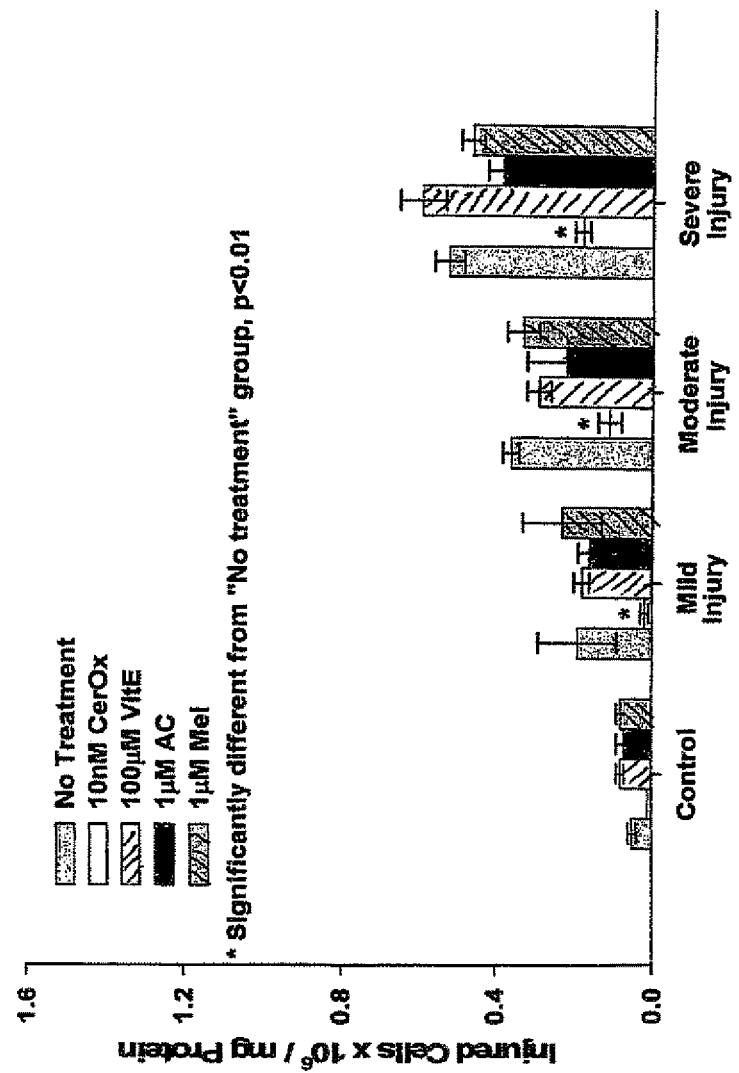
FIG. 21 shows the effect of cerium oxide nanoparticles against traumatic injury as compared to a single dose of other antioxidants when given pre-trauma.
Figure 22:
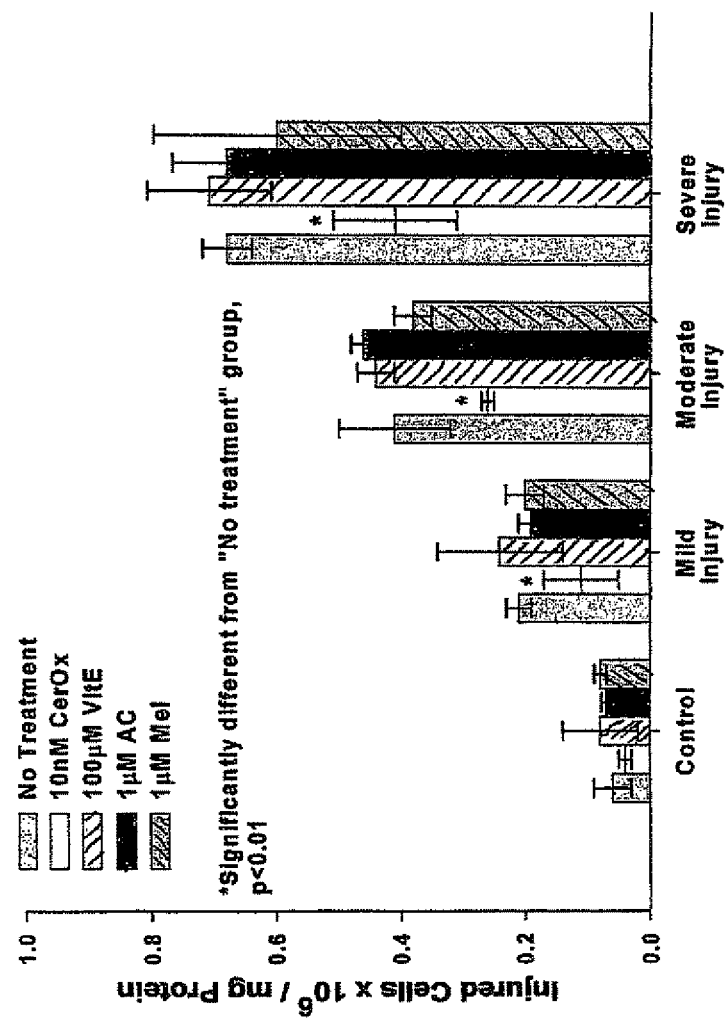
FIG. 22 shows the effect of cerium oxide nanoparticles against traumatic injury as compared to a single dose of other antioxidants when given post-tram-on FIG. 23 demonstrates the release of NO by astrocytes in both resting and injured states.

FIGS. 21 and 22 show that cerium oxide nanoparticles provide enhanced protection against traumatic injury as compared to a single dose of other antioxidants when given either pre-trauma (FIG. 21) or post trauma (FIG. 22). Using an in vitro model for traumatic brain injury (Ellis et al., J. Neurotrauma, 12, 325-339, 1995), we have previously shown that traumatic injury of mixed brain cell cultures produces cell death, in part, via generation of free radicals (Hoffman et al., Lamb, et al. J. Neurochem; 68, 1904-1910, 1997). Mixed brain cell cultures were injured at mild (5.5 mm), moderate (6.5 mm), and severe (7.5 mm) levels, and cell death was assessed with PrI, 24 hrs post injury.

FIGS. 23 to 26 show that cerium oxide nanoparticles decrease the release of NO from brain microglia. Pure cultures of astrocytes were injured using a well-characterized model for in vitro trauma. We have previously shown that exposure to medium conditioned by traumatically injured astrocytes induces microglial activation. MG so activated induce neuronal death. In these experiments microglia were activated by a 24 hour exposure to medium conditioned by mild, moderate, or severely injured astrocytes. Controls consisted of microglia exposed to medium conditioned by uninjured astrocytes. In these experiments, LPS was utilized as positive control. LPS, acting as an endotoxin, binds to receptors on microglia and triggers the secretion of pro-inflammatory cytokines and promotes the release of NO. Control or nano-treated microglia were exposed to 100 ng/ml LPS for 24 hours followed by measurement of NO released into the medium, as represented in FIG. 5. NO was measured using kits provided by Oxis International and Calbiochem, via. the Griess reaction. Absorbance was read in a BioTek ELx800 automated plate reader at 540 nm.

Figure 23:
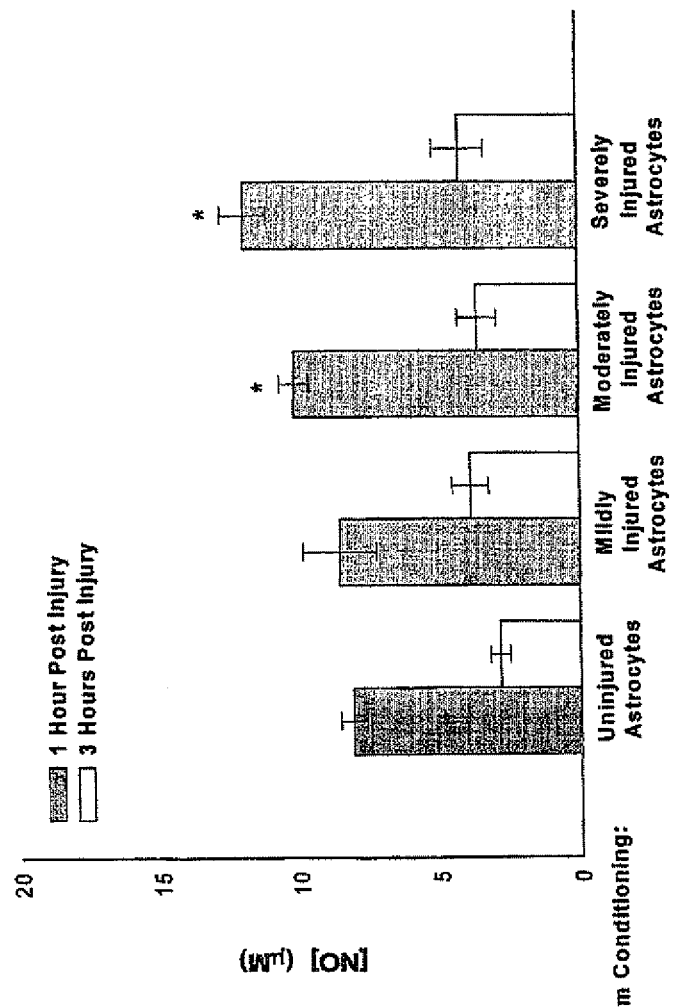

Because MG are activated by exposure to medium conditioned by injured astrocytes, we first determined NO release from astrocytes during the 1 and 3 hour post-injury period as shown in FIG. 23. There is significant NO release from moderate and severely injured astrocytes 1 hour after injury, suggesting that astrocytes play an important role in oxidative stress in the brain.

Figure 24:
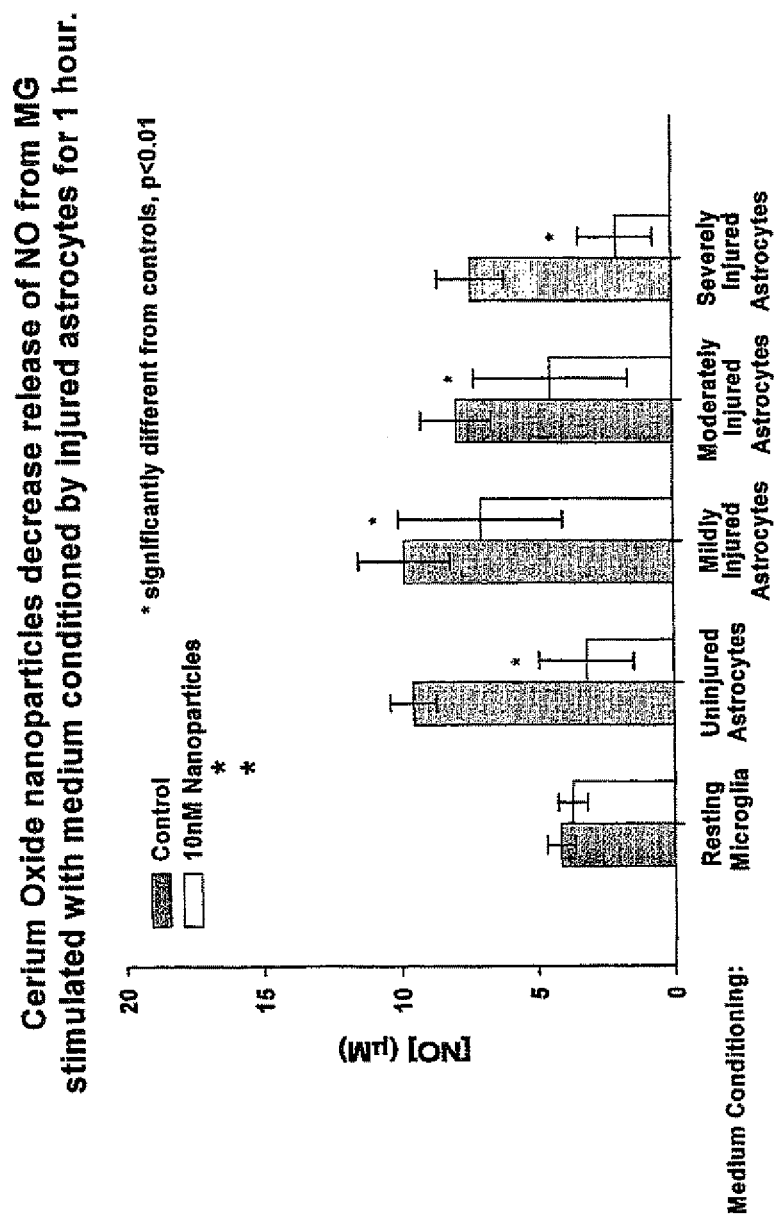
FIG. 24 shows the effect of cerium oxide nanoparticles on the release of NO from microglia stimulated with medium conditioned by injured astrocytes for 1 hour.
Figure 25:
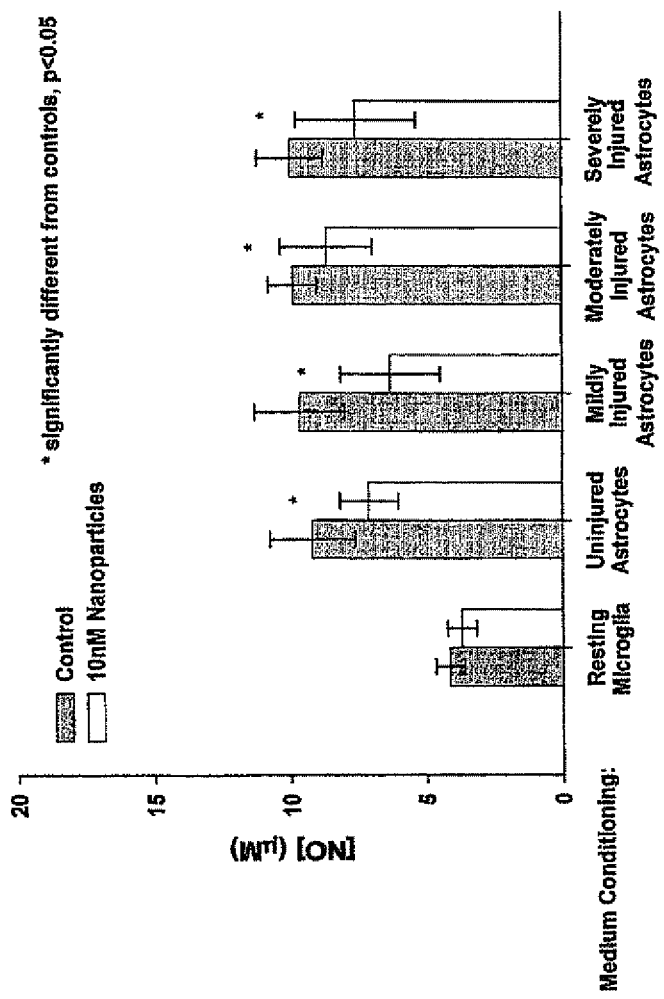
FIG. 25 shows the effect of cerium oxide nanoparticles on the release of NO from microglia stimulated with medium conditioned by injured astrocytes for 3 hours.

In FIGS. 24 and 25, exposure of MG to medium conditioned by astrocytes for 1 or 3 hours, regardless of injury, increased NO release, suggesting that astrocytes regulate the inflammatory potential of brain MG. Treatment of MG with 10 nM cerium oxide nanoparticles reduced NO release in all cases. In MG activated by exposure to medium conditioned by mild, moderate and severely injured astrocytes for 1 hour, cerium oxide nanoparticles reduced NO release by 29, 44, 70%, respectively. In MG activated by exposure to medium conditioned by mild, moderate and severely injured astrocytes for 3 hours, the decrease in NO release afforded by cerium oxide nanoparticles was more modest.

Figure 26:
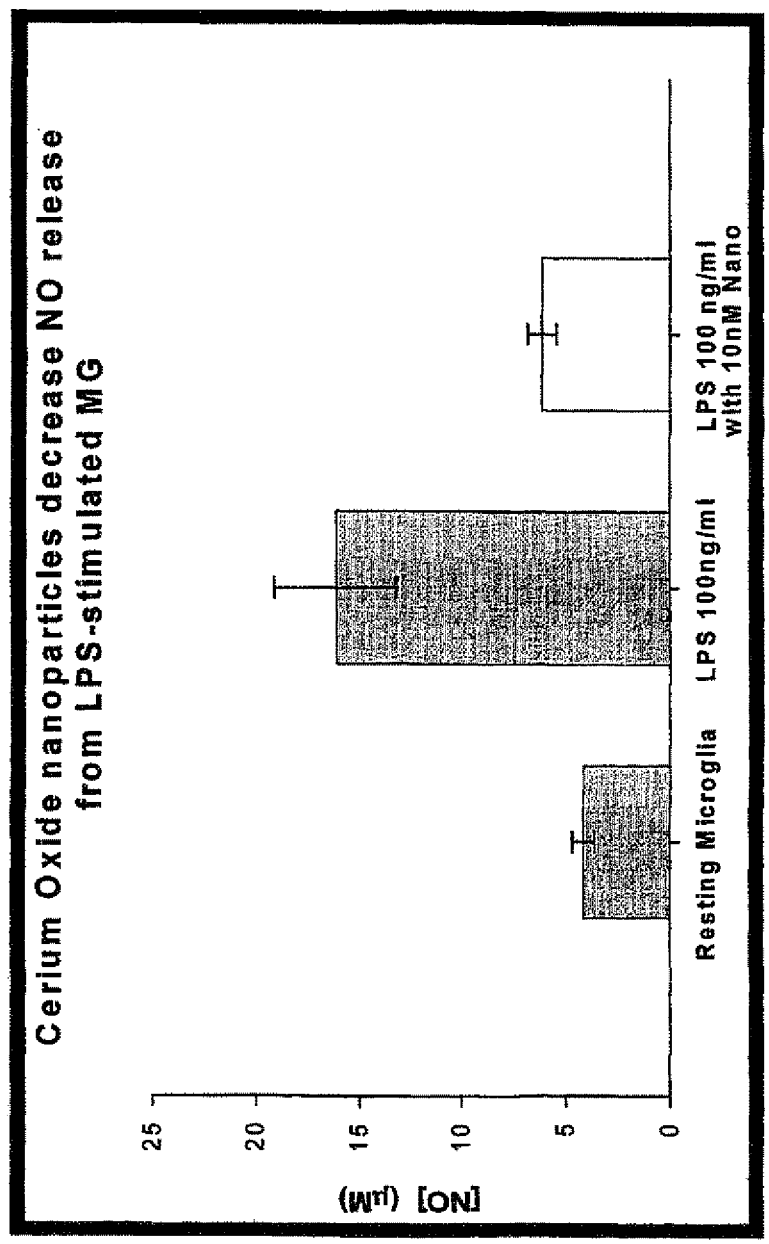
FIG. 26 shows the effect of cerium oxide nanoparticles on the release of NO from LPS-stimulated microglia.

In FIG. 26, MG exposed to 100 ng/ml LPS for 24 hours exhibited release of NO of 16.1 mM. When treated with 10 nM Cerium Oxide nanoparticles for 24 hours prior to exposure, NO release decreased by 62.0%, demonstrating that Cerium Oxide nanoparticles decrease release of inflammatory mediators that may enhance neuronal death.

Figure 27:
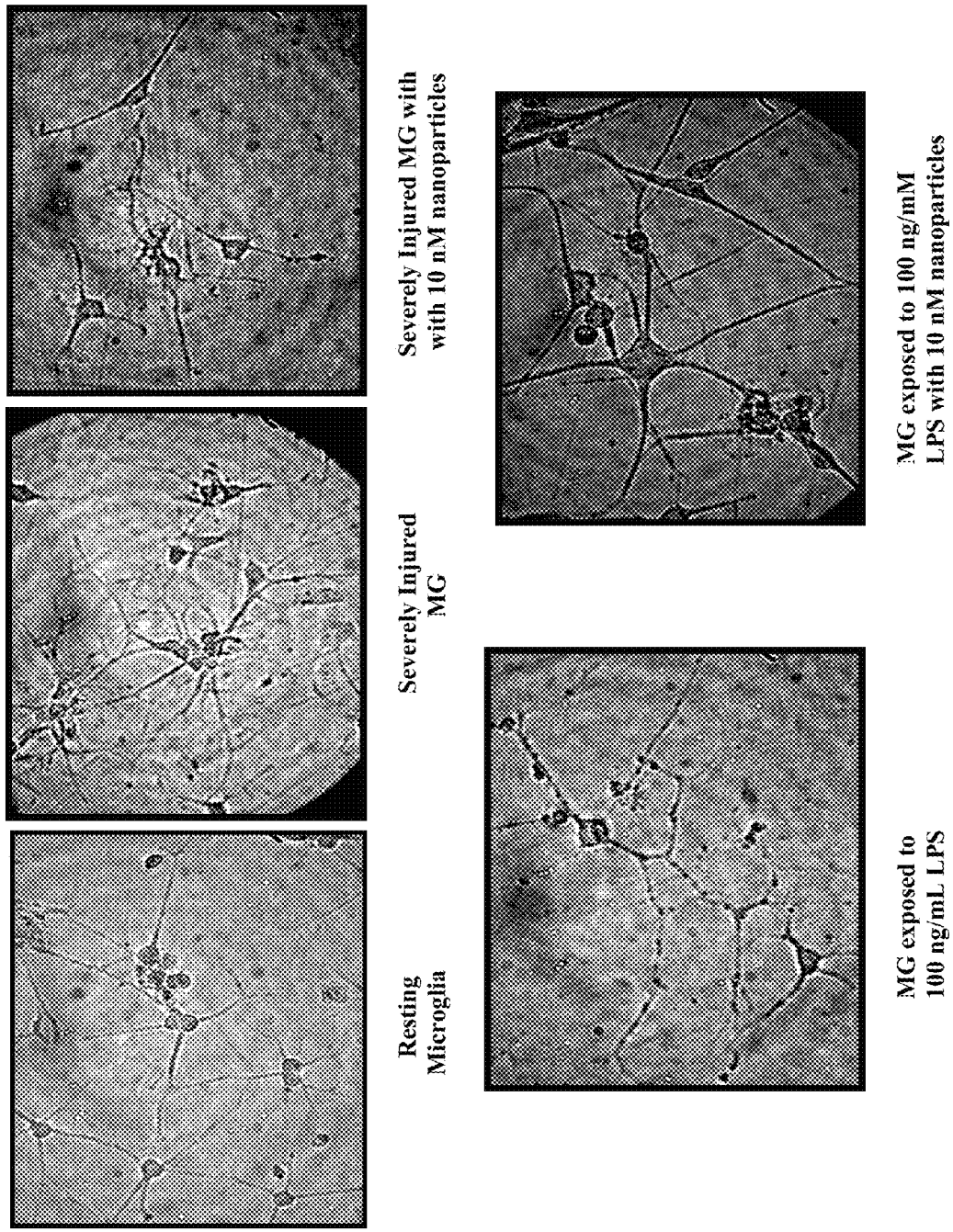
FIG. 27 demonstrates the morphology of microglia after injury or exposure to LPS with and without cerium oxide nanoparticles.

As shown in FIG. 27, resting MG have compact cell bodies with long, branched processes. MG activated by exposure to medium conditioned by severely injured astrocytes become more amoeboid in shape, with retracted, short processes and highly granulated and vacuolated cytoplasms. Pretreatment with Cerium Oxide nanoparticles prevent some of the morphological changes observed in. MG activation. MG were also stimulated with LPS. Note the dramatic morphological changes as compared to the resting state. LPS-induced morphological changes are blocked by Cerium Oxide nanoparticles.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

The invention claimed is:

1. A method for treating or reducing radiation injury to cells, said method comprising contacting the cells with 0.01 ng to about 1 g of cerium oxide nanoparticles having a size range of from 5 nm to 40 nm, wherein the cells have or will be exposed to high levels of radiation.

2. The method of claim 1, wherein the cerium oxide nanoparticles have a size range of from 5 nm to 25 nm.

3. The method of claim 1, wherein the cerium oxide nanoparticles have a size range of from 10 nm to 20 nm.

4. The method of claim 1, wherein 95% of the cerium oxide nanoparticles have a size from 5 nm to 25 nm.

5. The method of claim 1, wherein 90% of the cerium oxide nanoparticles have a size range from 10 nm to 20 nm.

6. The method of claim 1, wherein the cerium oxide nanoparticles have an average size of about 10 nm.

7. The method of claim 1, wherein the cells are exposed to radiation as part of a cancer treatment regimen.

8. The method of claim 7, wherein the cells are non-cancerous cells.

9. The method of claim 1, wherein exposure to radiation of the cells is associated with the work in the nuclear energy industry.

10. The method of claim 1, wherein the method is a method of reducing radiation injury to cells.

11. The method of claim 1, wherein the radiation is one or more of ultraviolet (UV), gamma radiation, beta radiation and X-ray radiation.

12. The method of claim 1, wherein the cerium oxide nanoparticles are produced from a process other than a sol-gel method.

13. The method of claim 1, wherein the act of contacting the cells with the cerium oxide nanoparticles occurs in vitro.

14. The method of claim 1, wherein the method is an in vivo method and the contacted cells consist of cells that are to be radioprotected in a subject.

15. The method of claim 14, wherein the cerium oxide nanoparticles are present in a composition that further comprises one or more of a sugar, salt, lipid, excipient, carrier, flavorant, filler, binding, gum, or colorant.

16. The method of claim 14, wherein the cerium oxide nanoparticles are present in a composition that further comprises one or more of water, a salt, buffered saline, or a lipid.

17. The method of claim 15, wherein the composition further comprises a nutritional supplement or dietary supplement for an animal.

18. The method of claim 14, wherein the subject is a human.

19. The method of claim 18, wherein the subject has a work environment with high radiation exposure.

20. The method of claim 14, wherein the cells are contacted with a sufficient amount of cerium oxide nanoparticles to provide blood levels of 10 nM to 1 µM of the cerium oxide nanoparticles.

21. The method of claim 1, wherein the cerium oxide nanoparticles are administered in a non-agglomerated suspension.

* * * * *